(12) United States Patent
Casey et al.

(10) Patent No.: US 10,456,173 B1
(45) Date of Patent: Oct. 29, 2019

(54) SYSTEMS AND METHODS FOR CORRECTING SPINAL DEFORMITIES

(71) Applicant: NuVasive, Inc., San Diego, CA (US)

(72) Inventors: Niall Casey, San Diego, CA (US); Robert German, San Diego, CA (US); Scott Lish, Oceanside, CA (US)

(73) Assignee: NuVasive, Inc., San Diego, CA (US)

( * ) Notice: Subject to any disclaimer, the term of this patent is extended or adjusted under 35 U.S.C. 154(b) by 139 days.

(21) Appl. No.: 15/359,365

(22) Filed: Nov. 22, 2016

Related U.S. Application Data

(63) Continuation of application No. 14/667,619, filed on Mar. 24, 2015, now Pat. No. 9,572,599, which is a continuation of application No. 12/945,821, filed on Nov. 12, 2010, now Pat. No. 8,986,349.

(60) Provisional application No. 61/390,561, filed on Oct. 6, 2010, provisional application No. 61/260,357, filed on Nov. 11, 2009.

(51) Int. Cl.
*A61B 17/70* (2006.01)
*A61B 17/86* (2006.01)

(52) U.S. Cl.
CPC ...... *A61B 17/7032* (2013.01); *A61B 17/7037* (2013.01); *A61B 17/8665* (2013.01); *A61B 2017/867* (2013.01)

(58) Field of Classification Search
CPC ............ A61B 17/7038; A61B 17/7032; A61B 17/7037
See application file for complete search history.

(56) References Cited

U.S. PATENT DOCUMENTS

| | | | |
|---|---|---|---|
| 929,067 A | 7/1909 | Williamson | |
| 1,841,647 A | 1/1932 | Smith | |
| 3,610,092 A | 10/1971 | Miller | |
| 4,577,837 A | 3/1986 | Berg et al. | |
| 5,176,678 A * | 1/1993 | Tsou | A61B 17/7032 606/267 |
| 5,288,161 A | 2/1994 | Graves et al. | |
| 5,318,388 A | 6/1994 | Papadopoulos | |
| 5,332,330 A | 7/1994 | Kaneko | |
| 5,499,983 A | 3/1996 | Hughes | |
| 5,545,166 A | 8/1996 | Howland | |
| 5,669,911 A | 9/1997 | Errico | |
| 5,672,176 A | 9/1997 | Biedermann | |
| 5,681,319 A | 10/1997 | Biedermann | |
| 5,683,392 A | 11/1997 | Richelsoph | |
| 5,690,630 A | 11/1997 | Erriro | |
| 5,816,633 A | 10/1998 | Odom | |
| 5,989,254 A | 11/1999 | Katz | |
| 6,063,090 A | 5/2000 | Schlapfer | |
| 6,074,391 A | 6/2000 | Metz-Stavenhagen et al. | |
| 6,174,110 B1 | 1/2001 | Papadopoulos | |
| 6,248,105 B1 | 6/2001 | Schalpfer | |
| 6,254,532 B1 | 7/2001 | Paolitto et al. | |
| RE37,665 E | 4/2002 | Ralph | |
| RE39,089 E | 5/2006 | Ralph | |
| 7,625,033 B2 | 12/2009 | Michelau et al. | |
| 7,655,008 B2 | 2/2010 | Lenke | |
| 7,678,137 B2 | 3/2010 | Butler | |
| 7,749,258 B2 | 7/2010 | Biedermann | |

(Continued)

*Primary Examiner* — Jacqueline T Johanas

(57) ABSTRACT

The present invention relates generally to medical devices and methods generally aimed at spinal surgery. In particular, the disclosed system and associated methods relate to performing spinal fixation with the use of a deformity system.

20 Claims, 31 Drawing Sheets

(56) References Cited

U.S. PATENT DOCUMENTS

| | | | |
|---|---|---|---|
| 7,766,944 B2 | 8/2010 | Metz-Stavenhagen | |
| 7,780,706 B2 | 8/2010 | Marino | |
| 7,794,464 B2 | 9/2010 | Bridwell | |
| 7,909,830 B2 | 3/2011 | Frigg et al. | |
| 7,942,909 B2 | 5/2011 | Hammill, Sr. | |
| 7,942,910 B2 | 5/2011 | Doubler | |
| 7,951,172 B2 | 5/2011 | Chao | |
| 7,951,173 B2 * | 5/2011 | Hammill, Sr. | A61B 17/7034 606/267 |
| 7,951,175 B2 | 5/2011 | Chao | |
| 7,972,364 B2 | 7/2011 | Biedermann | |
| 8,007,516 B2 | 8/2011 | Chao | |
| 8,007,522 B2 | 8/2011 | Hutchinson | |
| 8,012,186 B2 | 9/2011 | Pham | |
| 8,147,524 B2 | 4/2012 | Vallespir | |
| 8,177,817 B2 | 5/2012 | Fallin | |
| 8,197,518 B2 | 6/2012 | Hammill, Sr. | |
| 8,221,426 B2 | 7/2012 | Justis | |
| 8,277,453 B2 | 10/2012 | Kave | |
| 8,298,268 B2 | 10/2012 | Marino | |
| 8,308,774 B2 | 11/2012 | Hoffman et al. | |
| 8,333,770 B2 | 12/2012 | Hua | |
| 8,361,121 B2 | 1/2013 | Barry | |
| 8,465,529 B2 | 6/2013 | Choi | |
| 8,470,009 B1 | 6/2013 | Rezach | |
| 8,475,467 B2 | 7/2013 | Manninen | |
| 8,506,601 B2 | 8/2013 | Gephart et al. | |
| 8,636,783 B2 | 1/2014 | Crall | |
| 8,702,761 B1 | 4/2014 | Wang | |
| 8,961,568 B2 | 2/2015 | McKinley | |
| 8,998,965 B2 | 4/2015 | Biedermann | |
| 9,192,417 B2 | 11/2015 | Biedermann | |
| 2002/0032443 A1 | 3/2002 | Sherman | |
| 2003/0176861 A1 * | 9/2003 | Reed | A61B 17/6466 606/266 |
| 2003/0225408 A1 | 12/2003 | Nichols et al. | |
| 2003/0235463 A1 | 12/2003 | Neumann et al. | |
| 2004/0236330 A1 * | 11/2004 | Purcell | A61B 17/7037 606/266 |
| 2005/0137594 A1 | 6/2005 | Doubler et al. | |
| 2005/0222570 A1 | 10/2005 | Jackson | |
| 2006/0089651 A1 | 4/2006 | Trudeau et al. | |
| 2006/0111713 A1 | 5/2006 | Jackson | |
| 2006/0111714 A1 | 5/2006 | Foley | |
| 2006/0142761 A1 | 6/2006 | Landry et al. | |
| 2006/0155277 A1 | 7/2006 | Metz-Stavenhagen | |
| 2006/0161153 A1 | 7/2006 | Hawkes et al. | |
| 2006/0167454 A1 | 7/2006 | Ludwig et al. | |
| 2006/0173454 A1 | 8/2006 | Spitler et al. | |
| 2006/0173456 A1 | 8/2006 | Hawkes et al. | |
| 2006/0200131 A1 * | 9/2006 | Chao | A61B 17/7037 606/278 |
| 2006/0271050 A1 | 11/2006 | Piza Vallespir | |
| 2007/0032162 A1 | 2/2007 | Jackson | |
| 2007/0043364 A1 | 2/2007 | Cawley | |
| 2007/0078460 A1 | 4/2007 | Frigg et al. | |
| 2007/0088357 A1 | 4/2007 | Johnson | |
| 2007/0093827 A1 | 4/2007 | Warnick | |
| 2007/0161996 A1 | 7/2007 | Biedermann | |
| 2007/0162009 A1 * | 7/2007 | Chao | A61B 17/708 606/86 A |
| 2007/0225711 A1 | 9/2007 | Ensign | |
| 2007/0270842 A1 | 11/2007 | Bankoski et al. | |
| 2008/0091213 A1 | 4/2008 | Jackson | |
| 2008/0154277 A1 | 6/2008 | Machalk et al. | |
| 2008/0195159 A1 | 8/2008 | Kloss | |
| 2008/0243189 A1 * | 10/2008 | Purcell | A61B 17/7037 606/264 |
| 2008/0249576 A1 | 10/2008 | Hawkes et al. | |
| 2009/0157125 A1 | 6/2009 | Hoffman et al. | |
| 2009/0198280 A1 | 8/2009 | Spratt | |
| 2009/0228053 A1 | 9/2009 | Kolb | |
| 2009/0306721 A1 | 12/2009 | Kirschman | |
| 2010/0094306 A1 | 4/2010 | Chang et al. | |
| 2010/0137920 A1 * | 6/2010 | Hammill, Sr. | A61B 17/7034 606/308 |
| 2010/0160977 A1 | 6/2010 | Gephart et al. | |
| 2010/0305621 A1 | 12/2010 | Wang | |
| 2011/0106174 A1 | 5/2011 | Rezach | |
| 2011/0112585 A1 | 5/2011 | Biedermann | |
| 2011/0172714 A1 | 7/2011 | Adjei | |
| 2011/0208251 A1 | 8/2011 | Hammill, Sr. | |
| 2011/0257690 A1 | 10/2011 | Rezach | |
| 2011/0319938 A1 | 12/2011 | Vallespir | |
| 2012/0109224 A1 | 5/2012 | Biedermann | |
| 2013/0023941 A1 | 1/2013 | Jackson | |
| 2013/0096624 A1 | 4/2013 | Di Lauro | |
| 2013/0150904 A1 | 6/2013 | Biedermann | |
| 2013/0211458 A1 | 8/2013 | Rezach | |
| 2013/0226243 A1 | 8/2013 | Kraus | |
| 2014/0058463 A1 | 2/2014 | Biedermann | |
| 2015/0223484 A1 | 8/2015 | Shaffrey | |
| 2015/0282844 A1 | 10/2015 | Vedula | |
| 2016/0106472 A1 | 4/2016 | Di Lauro | |

* cited by examiner

SYSTEMS AND METHODS FOR CORRECTING SPINAL DEFORMITIES

CROSS-REFERENCES TO RELATED APPLICATIONS

This application is a continuation of U.S. patent application Ser. No. 14/667,619 (currently pending), filed Mar. 24, 2015, which is a continuation of U.S. patent application Ser. No. 12/945,821 (now U.S. Pat. No. 8,986,349), filed Nov. 12, 2010, which claims the benefit of priority from U.S. Provisional Patent Application Ser. No. 61/260,357, filed on Nov. 11, 2009, and U.S. Provisional Patent Application Ser. No. 61/390,561, filed on Oct. 6, 2010, the entire contents of which are hereby expressly incorporated by reference into this disclosure as if set forth in their entireties herein.

FIELD

The present invention relates generally to medical devices and methods generally aimed at spinal surgery. In particular, the disclosed system and associated methods relate to performing spinal fixation with the use of a deformity system.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the sacral and coccygeal regions of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g. walking, talking, and breathing, etc. . . . ). Therefore, it is of great interest and concern to be able to both correct and prevent any ailments of the spine.

Fixation systems are often surgically implanted into a patient to aid in the stabilization of a damaged spine or to aid in the correction of other spinal geometric deformities. Spinal fixation systems are often constructed as framework stabilizing a particular section of the spine. Existing systems often use a combination of rods, plates, pedicle screws and bone hooks for fixing the framework to the affected vertebrae. The configuration required for each patient varies due to the patient's specific anatomical characteristics and ailments. As a result, there is a need for a modular spinal fixation system that allows for a large degree of custom configurations and that can assist the clinician in the corrective maneuvers often needed to rehabilitate severe deformities.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal anchor assembly disclosed herein boasts a variety of inventive features and components that warrant patent protection, both individually and in combination.

Figure 1:
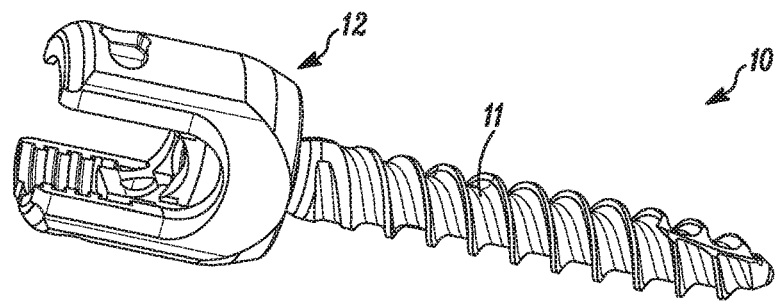
FIG. 1 is a perspective view of a spinal anchor assembly according to one example embodiment.

FIG. 1 illustrates an example of a spinal anchor assembly 10 according to a first embodiment of the present invention. The spinal anchor assembly 10 includes a bone screw 11 and a receiver assembly 12. A closure structure 13 (shown in FIGS. 5-7) is used to capture a rod within the receiver assembly 12. The spinal anchor assembly 10 and closure structure 13 are composed of a metal (e.g. titanium, stainless steel, etc.).

The bone screw 11 of the present invention is configured to attach securely within a bony structure (e.g. pedicle of a vertebra) and to allow the receiver assembly 12 to provisionally lock into position relative to the bone screw 11 after placement of the bone screw 11 within a bony structure. The receiver assembly 12 and bone screw 11 are configured to engage with full polyaxial motion. The receiver assembly 12 and bone screw 11 can also be provisionally locked (that is, fixed relative to each other prior to final capture and locking of a spinal rod into the receiver), as will be described in more detail below. This versatile engagement between the receiver assembly 12 and bone screw 11 provides both the ease of positioning and rod placement associated with polyaxial screws and the ability to leverage the bone anchor 10 to manipulate the vertebral body (e.g. parallel distraction and compression and/or vertebral body derotation) associated with fixed-axis anchors.

By way of example, the bone screw 11 of the spinal anchor assembly 10 may be engaged within a pedicle of a vertebra and aligned with a spinal rod connecting other anchors. A clinician may then engage an instrument to the receiver assembly 12 and provisionally lock the screw 11 and receiver 12. With the screw locked, the clinician can utilize the instrument to apply a force upon the vertebra to correct the deformity prior to fixing the construct and thus the spinal column in a desired position. The ability to utilize the spinal anchor assembly 10 to reposition segments of the spine to correct deformities simplifies the procedure for the clinician by limiting the amount of tools and time required.

Figure 2:
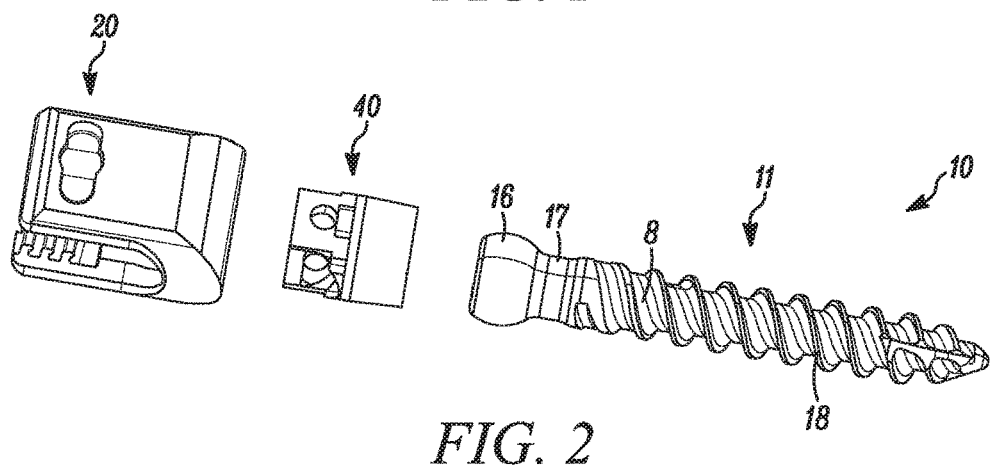
FIG. 2 is an exploded view of the spinal anchor assembly of FIG. 1.
Figure 3:
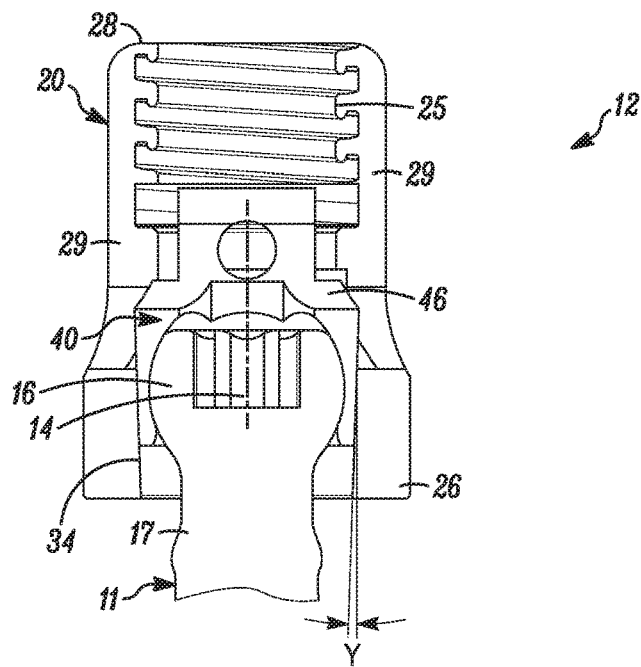
FIG. 3 is a partial cross section view of the spinal anchor assembly of FIG. 1.

With reference to FIGS. 1-3, the bone screw 11 of the spinal anchor assembly 10 is comprised of a shank 17, a body 8, and a capture structure 16. At least one helically-wound bone implantable thread 18 extends radially from the body 8 and functions to secure the placement of the bone screw 11 within a bony structure. The capture structure 16 includes at least one tool engaging feature 14 that can be used, for example, to engage and attach various tooling for aligning and advancing the bone screw 11 into a bony structure. The generally spherical shape of the capture structure 16 allows it, for example, to articulate within the collet 40 to achieve the polyaxial motion between the bone screw 11 and the receiver assembly 12. The surface of the capture structure 16 may be textured (e.g. scored or knurled) for enhancing frictional engagement with the collet 40 that secures the positioning of the bone screw 11 relative to the receiver assembly 12.

The receiver assembly 12 is configured to receive an elongate structure (e.g. a rod) and the closure structure 13 is designed to secure the rod within the receiver assembly 12. Once the receiver assembly 12 and bone screw 11 are securely oriented in the desired orientation and the rod is captured in the receiver assembly 12, the closure structure 13 can be engaged to lock the rod in the receiver assembly 12.

The receiver assembly 12 is typically provided in an assembled state (best shown in FIG. 3) and includes a receiver 20 and a retaining and articulating structure or collet 40. The receiver 20 has a generally U-shaped appearance with a generally cylindrical inner profile and a faceted outer profile. A base 26, with a pair of upstanding arms 29 forms a U-shaped cradle which define U-shaped openings 27 through the faceted sides of the receiver 20. Receivers may be provided in a variety of dimensions depending on the size and shape of the rod that it will be in secured frictional engagement with.

Both arms 29 have at least one helically-wound guide and advancement structure 25 at least partially situated along their internal walls beginning from the top surface 28 end of the receiver 20. The guide and advancement structure 25 of the receiver 20 are configured to mate with at least one exterior helically-wound guide and advancement structure 72 of the closure structure 13. When the internal and external guide and advancement structures 25, 72 of the closure structure 13 and receiver 20 are interlocked, their connection prevents the arms 29 of the receiver 20 from spreading open due to the mating features of the guide and advancement structures 25 and 72. This interlocked configuration prevents splaying of the arms 29.

Figure 4:
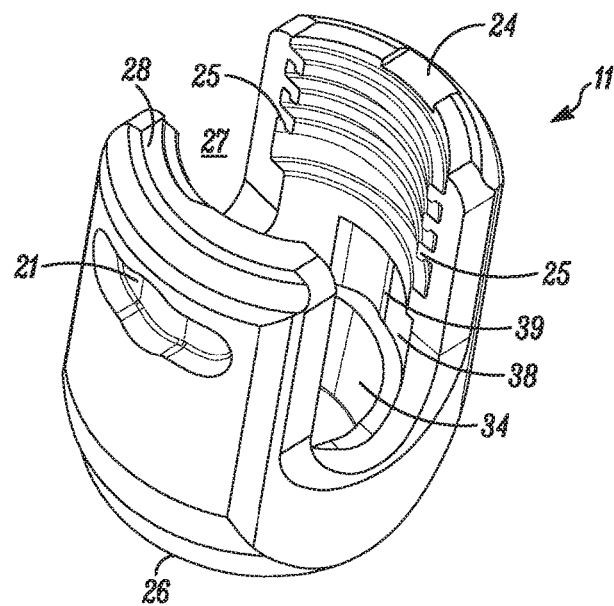
FIG. 4 is a perspective view of the receiver forming a part of the spinal anchor assembly of FIG. 1.

As illustrated in FIG. 4, the outer surface of the receiver 20 includes tooling attachment features, such as grip bores 21, on the outer surface of both arms 29 which function to allow a variety of tools to engage the receiver assembly 12 for subsequent positioning and implantation of the spinal anchor assembly 10. Additional features of the receiver 20 include two sweeping steps 38 recessed inwardly from the inside walls of the arms 29 (with one sweeping step 38 situated on each arm 29). The sweeping steps 38 are utilized during the assembly of the receiver assembly 12 by allowing the locking ledges 55 of the collet 40 to be guided into position within the receiver 20. Once the collet 40 is assembled within the receiver 20, the collet 40 is allowed limited movement. By way of example, each sweeping step 38 includes a notch 39 that prevents the locking ledge 55 from backing out of the sweeping step 38 once it has traveled past the notch 39. Additionally, the top and bottom walls of each sweeping step 38 restricts the longitudinal translation of the collet 40 relative to the receiver by restricting the longitudinal translation of the locking ledge to only between the top and bottom walls of the sweeping step 38. By way of example only, each sweeping step 38 spans at least a portion of the inside wall of an arm 29 and are positioned generally 180 degrees apart from one another.

Located within the base 26 of the receiver 20 is a tapered cavity 34 that is sized and shaped for slidable mating and eventual frictional engagement with the tapered feature 48 of the collet 40, as will be described in more detail below. By way of example only, the tapered cavity 34 may have a taper of approximately 2-3 degrees (shown as angle Y in FIG. 3). The taper feature 48 of the collet 40 is shown as angle Z in FIG. 10. When the collet 40 is forced generally in the direction of the base 26 of the receiver 20 along its longitudinal axis, the tapered feature 48 of the collet will become frictionally secured (wedged) within the tapered cavity 34.

Figure 8:
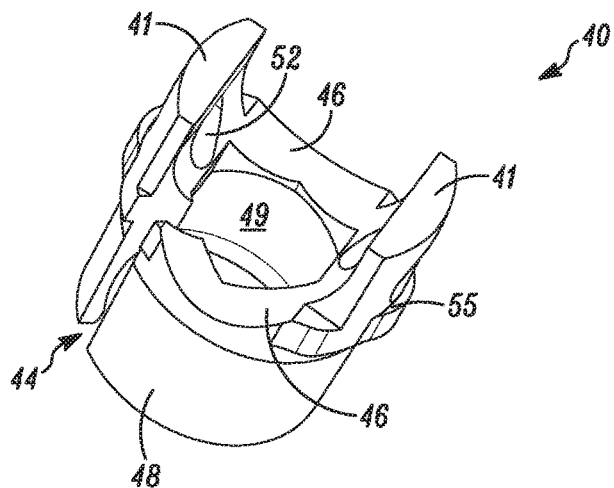
FIG. 8 is a perspective view of a collet forming part of the receiver assembly of FIG. 1.
Figure 9:
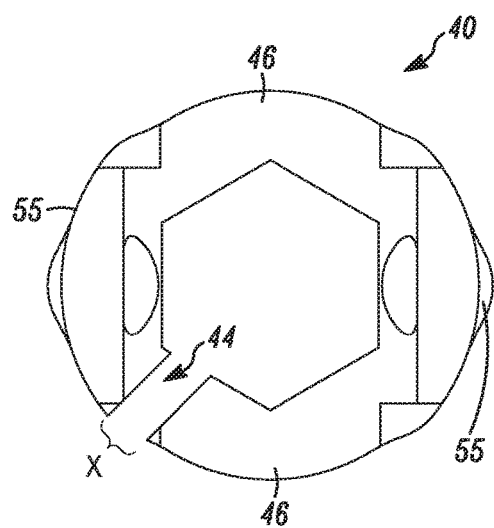
FIG. 9 is a top view of the collet forming part of the receiver assembly of FIG. 1.
Figure 10:
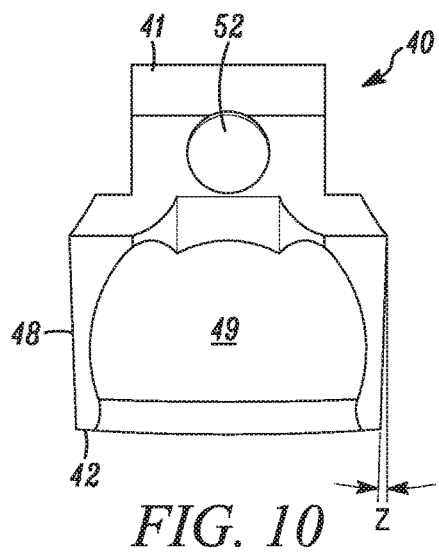
FIG. 10 is side view of the collet forming part of the receiver assembly of FIG. 1.

FIGS. 8-10 illustrate an example of a collet 40 according to a first embodiment. The collet 40 includes a top surface 41, a bottom surface 42, an inner spherical surface 49, a tapered feature 48, locking ledges 55, a saddle 46, and a tooling engagement feature 52. Notably, the collet 40 is not continuous, and instead includes a slot 44. The slot 44 is dimensioned to be a distance X (best shown in FIG. 9) and allows the collet 40 to be temporarily expanded or compressed to receive the capture structure 16 and to secure the capture structure 16 within the inner spherical surface 49.

During assembly of the spinal anchor assembly 10, the collet 40 receives, and permanently captures, the capture structure 16 within the inner spherical surface 49. Once the capture structure 16 is captured within the inner spherical surface 49, the collet 40 and associated bone screw 11 is assembled to the receiver 20. This is accomplished by leading the distal end of the bone screw 11 through the center of the receiver until the locking ledges 55 are aligned with the sweeping step 38 of the receiver 20. As described above, the locking ledges 55 travel along the sweeping steps 38 until they pass the notch 39, where the collet 40 then becomes permanently limited in movement relative to the receiver 20. At this point, the collet 40 is able to travel a limited distance along its longitudinal axis. Additionally, the bone screw 11 is able to articulate relative to the receiver assembly 12 achieve poly axial motion of the receiver assembly. By way of example, the bone screw 11 is able to articulate and form an angle between its longitudinal axis and the longitudinal axis of the receiver 20 of up to approximately 20 degrees in any direction. When the desired angular orientation is achieved, the receiver assembly 12 is locked into position relative to the bone screw 11. For this to occur, the collet 40 is wedged into the receiver 20 which compresses the slot 44 and causes the inner spherical surface 49 to frictionally engage and secure the capture structure 16. This permanently fixes the configuration of the receiver 20, collet 40, and bone screw 11.

As discussed, the anchor assembly 10 can be both provisionally locked and finally locked. By way of a first example, the spinal anchor assembly 10 can be finally locked by driving a rod (e.g. rod 60) into the collet 40 and receiver 20 by engaging and advancing a closure structure 13 into the receiver 20. As the closure structure 13 advances, the rod is forced down into the collet 40 and the collet 40 in turn is driven down and wedges into the tapered cavity 34. At this point, the collet 40 is locked into position relative to the receiver 20 and the rod is securely locked between the closure structure 13 and collet 40.

The spinal anchor assembly 10 can be provisionally locked by fully reducing the rod 60) into the collet 40 and receiver 20 with an instrument, such as the reduction tower 900 (described below). The reduction tower 900 releasably attaches to the receiver 20 and an arm directs the rod 60 into the receiver 20, forcing the rod into the collet 40 which is driven down and wedges into the tapered cavity 34. At this point, the collet 40, receiver 20, and bone screw 11 are locked into position relative to each other, however, the rod is not locked within the receiver assembly 12, and the bone anchor can be used to adjust the position or orientation of the vertebra to which the anchor assembly 10 is attached (e.g. parallel distraction and compression or derotation). The closure structure 13 can be advanced in to the receiver 20 when it becomes desirable to secure the rod within the receiver assembly 12.

By way of another example, the spinal anchor assembly 10 can be provisionally locked by driving a rod-like tooling feature into the rod into the collet 40. Again, this provisional locking feature provides a platform for the clinician to utilize the screw to manipulate the position or orientation of the vertebra while still allowing the receiver to be adjusted for easier reception of the rod.

The tooling engagement features 52 of the collet 40 allow the user to unlock the anchor assembly 10 from the provisionally locked configuration, if necessary. A tool can engage the tooling engagement features 52 to, for example, compress and/or pull on the collet 40 in order to release the frictional engagement between the tapered feature 48 of the collet 40 and tapered cavity 34 of the receiver 20.

The saddle 46 of the collet 40 provides a contouring surface for mating with a rod within the receiver assembly 12. By way of example only (and best shown in FIG. 8), the saddle 46 has two U-shaped surfaces that are generally shaped to receive a rod. The saddle 46 may be any number of shapes and sizes necessary to accommodate a particular rod, without departing from the scope of this invention. Furthermore, the shape and dimensions of the collet 40 and its features may be any number of shapes and dimensions without departing from the scope of this invention.

Figure 5:
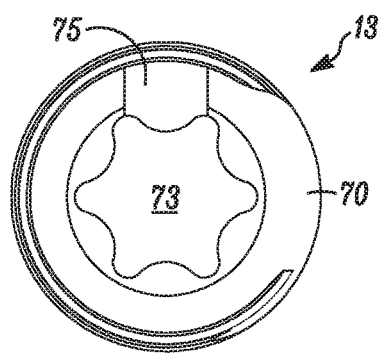
FIG. 5 is a top view of one example of a closure structure.
Figure 6:
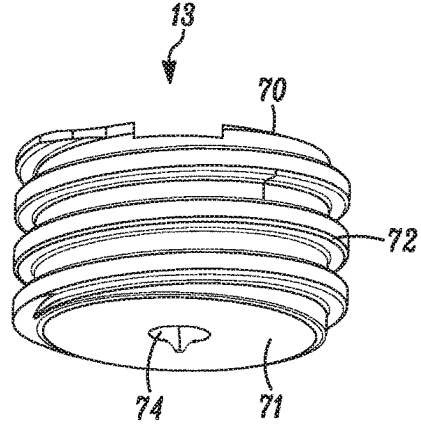
FIG. 6 is a perspective view of the closure structure of FIG. 5.
Figure 7:
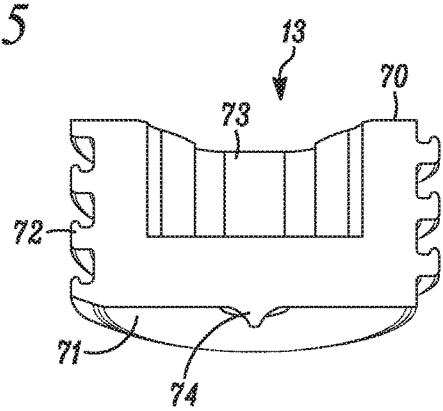
FIG. 7 is a perspective cross section view of the closure structure of FIG. 5.

FIGS. 5-7 illustrate one example embodiment of a closure structure 13. The closure structure 13 is shown by way of example to include a top surface 70, a base 71, and at least one exterior guide and advancement structure 72. The top surface 70 includes at least one generally recessed tool engaging feature 73 which functions to engage a variety of tooling that assist in aligning and securing the closure structure 13 to the receiver assembly 12. A recessed slot 75 on the top surface 70 functions to provide the clinician with an aligning mechanism for screwing the closure structure 13 into the receiver 20. For example, the recessed slot 75 of the closure structure 13 should be aligned with the recessed slot 24 of the receiver 20 prior to advancing the closure structure 13 to facilitate proper engagement. Positioned centrally within the base 71 of the closure structure 13 is a point force feature 74 that applies a point force to secure a portion of an rod (e.g. rod 60). The point force feature 74 deforms upon final tightening of the screw and improves resistance to translation and centers the locking stress within the receiver 12. It will be appreciated that while the closure structure 13 shown may be preferred, closure structures utilizing a number of other suitable structures and features may be utilized without departing from the scope of this invention.

Figure 11:
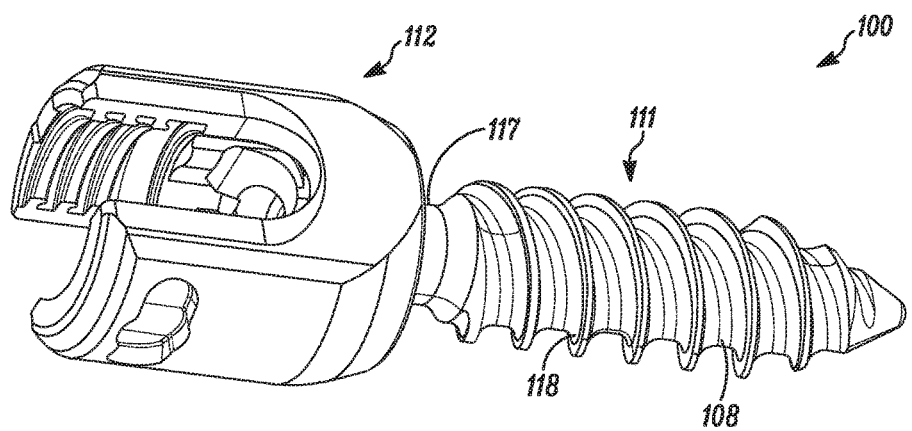
FIG. 11 is a perspective view of another spinal anchor assembly according to a second example embodiment.

FIG. 11 illustrates an example of a spinal anchor assembly 100 according to a second embodiment of the present invention. The spinal anchor assembly 100 includes a bone screw 111 and a receiver assembly 112. By way of one example, a closure structure 13 (shown in FIGS. 5-7) is used to capture a rod within the receiver assembly 112. The spinal anchor assembly 100 is preferably composed of a metal (e.g. titanium, stainless steel, etc.).

The spinal anchor assembly 100 of the present invention is available to a clinician in a pre-assembled state such that the receiver assembly 112 is jointly attached to the capture structure 116 of the bone screw 111. The receiver assembly 112 and bone screw 111 are able configured to engage with limited axial movement. More specifically, the receiver member 112 may articulate along a single plane (i.e. uniplanar movement), and can ultimately be secured at any number of angles within the single plane. Similar to the provisional locking anchor assembly 10, the uniplanar engagement between the receiver assembly 112 and the bone screw 111 permits some flexibility for positioning the rod, while still providing the ability to leverage the anchor assembly to manipulate the vertebra to correct positioning and alignment of the vertebra. By way of example, the anchor assembly may be implanted such that the articulating plane is the sagittal plane (i.e. movement is cranial-caudal). Positioned as such, force may be applied to the screw in the transverse plane (i.e. medial/lateral direction) to derotate a vertebra. One advantage of limiting the angled articulation between the receiver assembly 112 and bone screw 111 to only along a single plane is so that force can be applied upon the spinal anchor assembly 100 in any direction that is along a non-articulating plane. By way of example, the bone screw 111 of the spinal anchor assembly 100 would be first secured within a pedicle of a vertebra. A clinician may engage an instrument to the receiver assembly 112 and to apply the correcting force.

Figure 12:
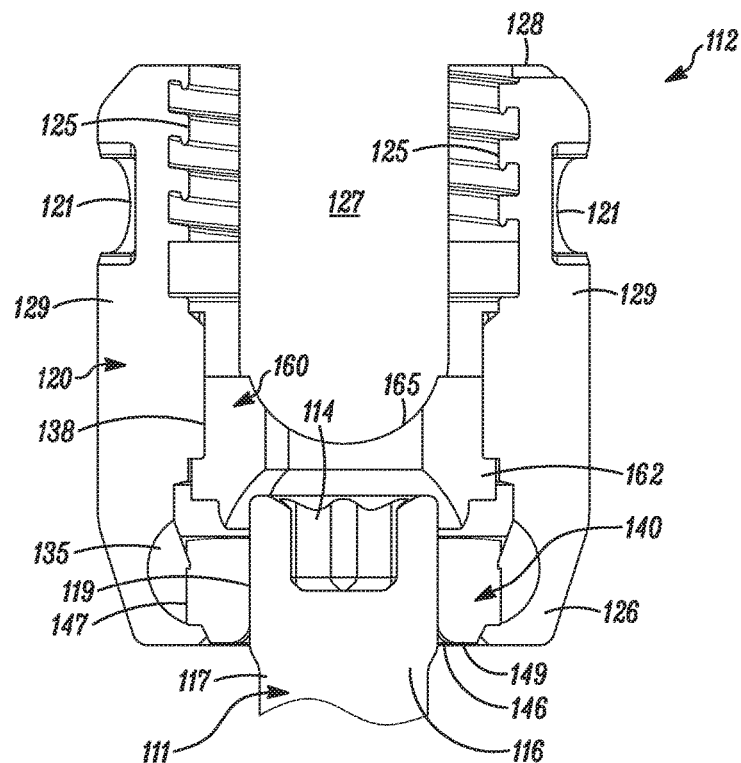
FIG. 12 is a partial cross section view of the spinal anchor assembly of FIG. 11.
Figure 13:
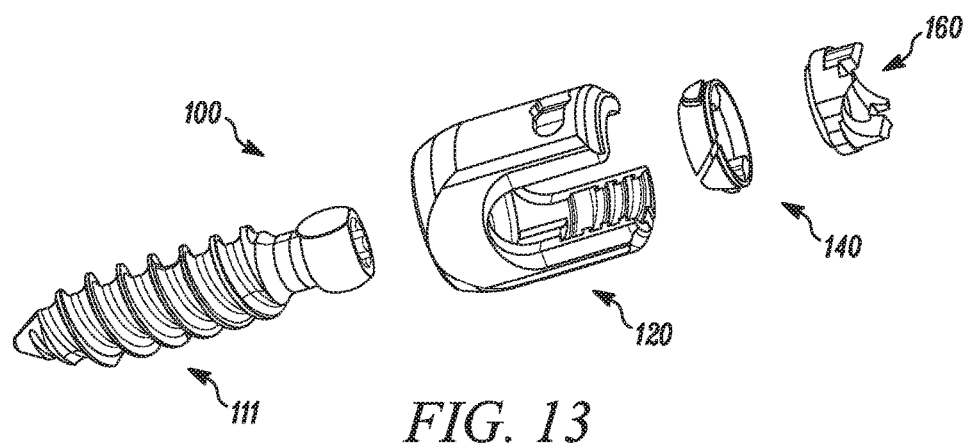
FIG. 13 is an exploded view of the spinal anchor assembly of FIG. 11.
Figure 14:
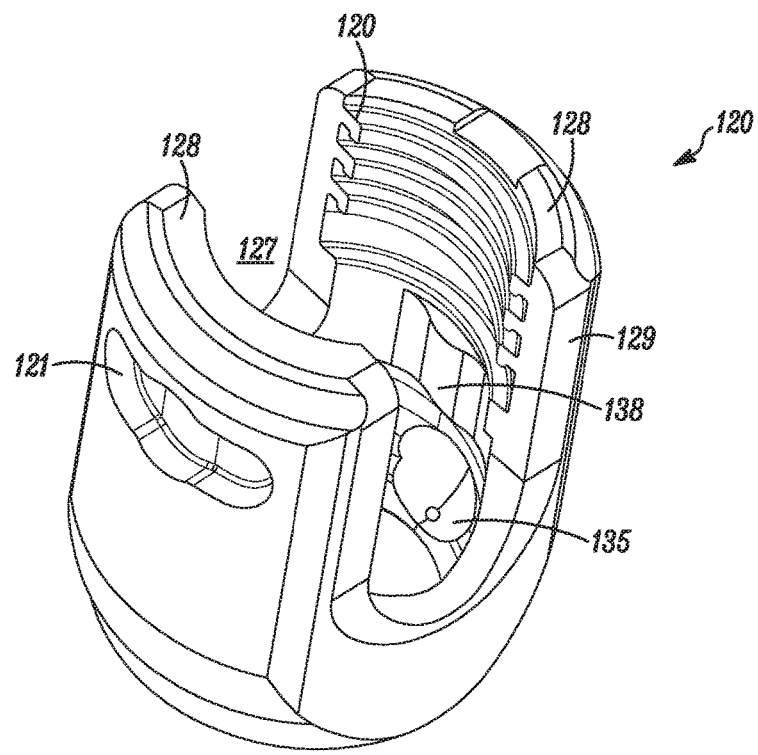
FIG. 14 is a perspective view of the receiver forming a part of the spinal anchor assembly of FIG. 11.

With reference to FIGS. 11-13, the spinal anchor assembly 100 is comprised of a shank 117, a body 108, and a capture structure 116. At least one helically-wound bone implantable thread 118 extends radially from the body 108 and functions to secure the placement of the bone screw 111 within a bony structure. Additionally, the capture structure 116 includes flat surfaces 119 on opposing sides of the capture structure 116. The flat surfaces 119 restrict rotation between the bone screw 111 and the collar 140 to the plane parallel to the flat side 19. Preferably, the articulating plane is aligned with the side openings 127 such the uniplanar movement is in line with the rod.

The capture structure 116 includes at least one tool engaging feature 114 that can be used, for example, to engage and attach various tooling for aligning and advancing the bone screw 111 into a bony structure. The generally spherical shape portions of the capture structure 116 allow the capture structure 116, for example, to articulate within the collar 140 along a single plane. The surface of the capture structure 116 may be textured (e.g. scored or knurled) for enhancing frictional engagement with the collar 140, which assists in securing the position of the bone screw 111 relative to the receiver assembly 112, as will be discussed in more detail below.

FIG. 12 illustrates an example embodiment of a receiver assembly 112. The receiver assembly 112 is typically provided in an assembled state (as shown in FIGS. 11 and 12) and includes a receiver 120, a retaining and articulating structure or collar 140, and a cradle 160. The receiver 120 has a generally U-shaped appearance with a generally cylindrical inner profile and a faceted outer profile. A base 126, with a pair of upstanding arms 129 forms a U-shaped cradle which define U-shaped openings 127 through the faceted sides of the receiver 120. Alternatively, receiver 120 may be provided with openings having any of a variety of shapes and dimensions depending, in part, on the size and shape of the rod to be received.

Both arms 129 have at least one helical wound guide and advancement structure 125 at least partially situated along their internal walls beginning from the top surface 128 end of the receiver 120. The guide and advancement structure 125 of the receiver 120 are configured to mate with at least one exterior helically-wound guide and advancement structure of a closure structure (not shown in this embodiment), which assist in preventing the arms from spreading open. The closure structure 13 described in the anchor assembly 10 may be used with anchor assembly 110 to secure a portion of a rod within a receiver assembly 112. Again, it should be appreciated that while the closure structure 13 shown may be preferred, closure structures utilizing a number of other suitable structures and features may be utilized without departing from the scope of this invention.

The outer surface of the receiver 120 includes tooling attachment features, such as grip bores 121, on the outer surface of both arms 129. Grip bores 121 function, for example, to allow a variety of tools to engage the receiver assembly 112 for subsequent implantation and positioning of the receiver assembly 112 and spinal anchor assembly 100. Additional features of the receiver 120 include two steps 138 extending inwardly from the inside walls of the arms 129 (with one step 138 situated on each arm 129). By way of example only, each step 138 spans at least a portion of the inside wall of an arm 129 and is positioned generally 180 degrees apart from the other. Located within the base 126 end of the receiver 120 is a cavity that is defined by a generally spherical surface and is sized and shaped for slidable mating and eventual frictional engagement with the retaining and articulating structure or collar 140, as described below. Along the walls of the cavity within the base 126 of the receiver is a pair of rounded pivot features 135. The rounded pivot features 135 are located approximately 180 degrees apart from one another the wings 147 of the collar 140 and permit the collar 140 to articulate generally along a single plane.

Figure 15:
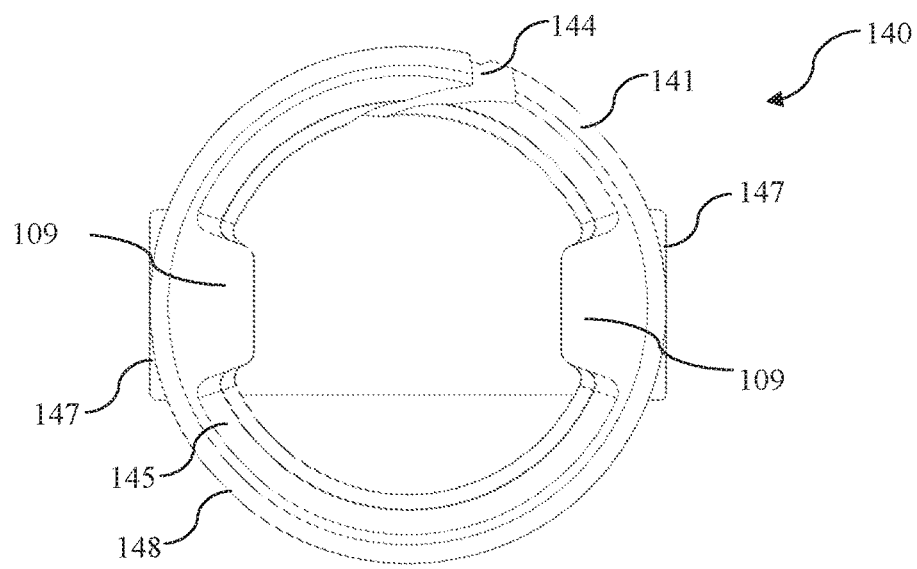
FIG. 15 is a top view of the collar forming part of the receiver assembly of FIG. 11.
Figure 16:
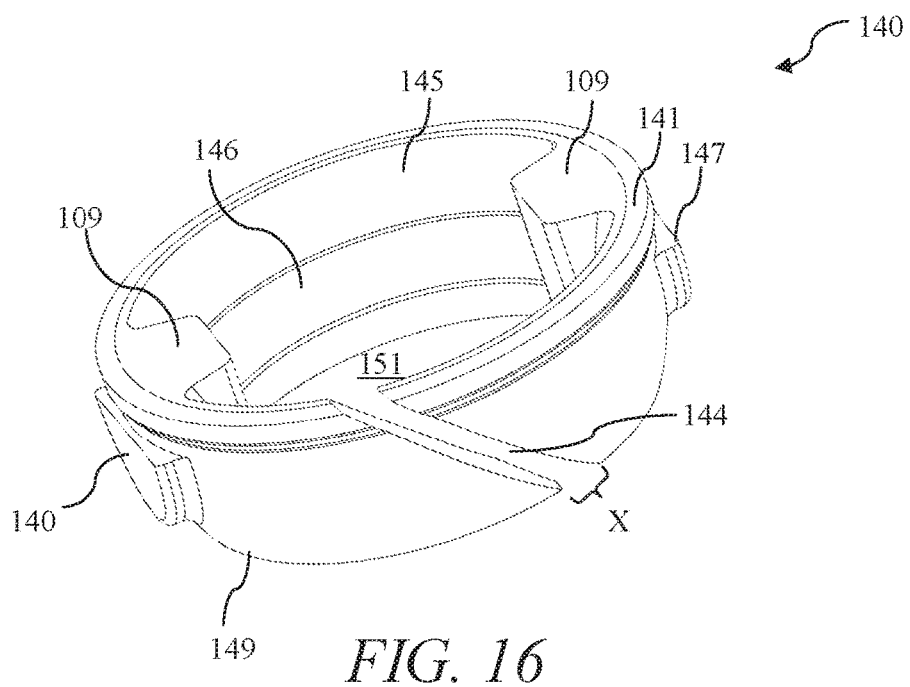
FIG. 16 is a perspective view of the collar of FIG. 15.

FIGS. 15-16 illustrate an example of an embodiment of a retaining and articulating structure or collar 140. The collar 140 is comprised of a top surface 141, a bottom surface 149, an outer convex surface 152, an inner concave surface 145, and a radial protrusion 148. Notably, the collar 140 is not continuous, and instead includes a slot 144 extending from the top surface 141 to bottom surface 149. The length of the slot 144 is dimensioned to be a distance X (best shown in FIG. 16) and allows the collar 140 to be temporarily expanded or compressed to secure the collar 140 around the capture structure 160, as described below.

Wings 147 protrude from opposing sides of the outer convex surface 152 of the collar 140. The wings 147 are sized and shaped to mate with the pivot feature 135 of the receiver 120. By way of example, the wings 147 may be D-shaped, but may be any size and shape suitable for directing and limiting the pivot direction of the collar 140 (and associated bone screw 111). When mated, the wings 147 assist in both positioning the collar 140 within the receiver 120 and restricting the pivot directions of the collar 140 to along a single plane. The wings 147 also restrict relative rotation between the collar 140 and receiver 120 along their longitudinal axis. The bone screw 111 and associated collar 140 are able to pivot relative to the receiver 120 along a single plane for subsequent secure positioning and implantation. Interior protrusions 109 extend inwardly from opposing sides of the inner concave surface 145 of the collar 140. The interior protrusions 109 function to mate with the flat surfaces 119 on a capture structure 116 to prevent the rotation of a bone screw 111 relative to the collar 140 along their longitudinal axis.

Figure 17:
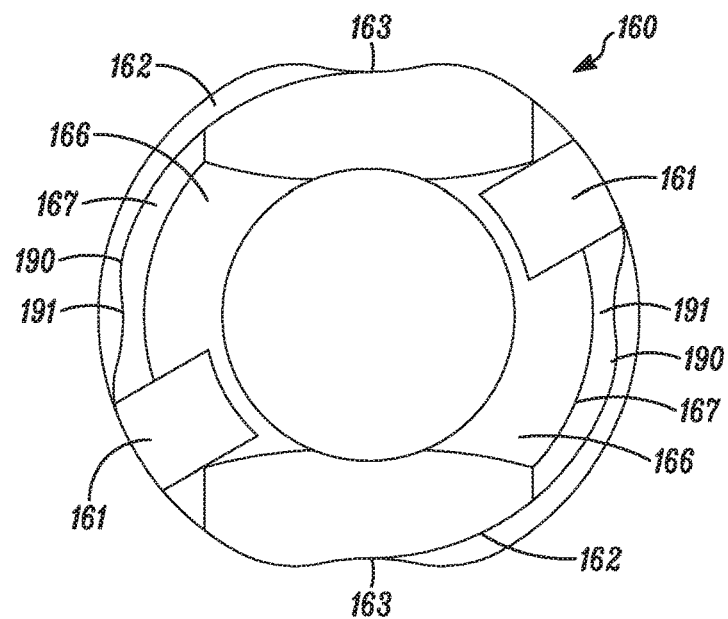
FIG. 17 a top view of the cradle forming part of the receiver assembly of FIG. 11.
Figure 18:
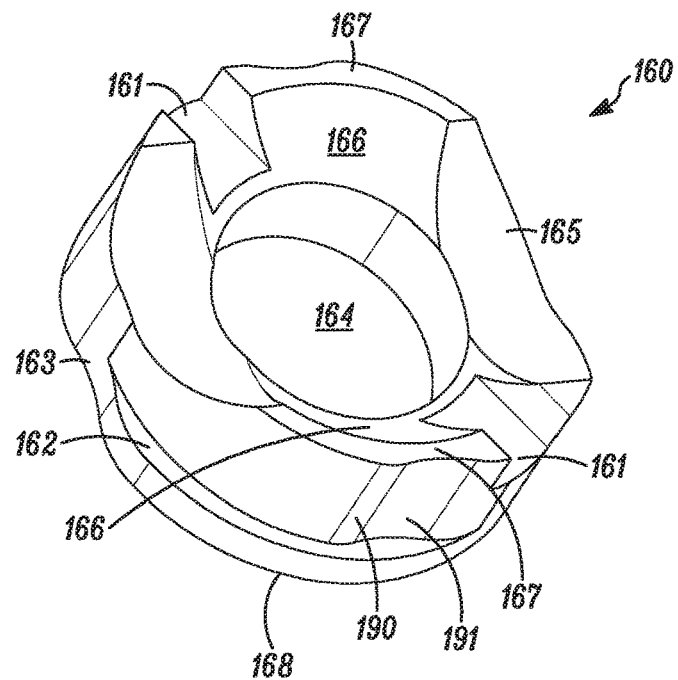
FIG. 18 is a perspective view of the cradle of FIG. 17.

FIGS. 17-18 illustrate an example embodiment of a cradle 160. The cradle 160 is comprised of a top surface 167, spherical inner walls 166, concave supports 165, and a base 168. Additional features of the cradle 160 include first outer diameter notches 163, second outer diameter notches 191, locking protuberances 190, a central opening 164, locking ledges 162, and tool engaging features 161. As previously noted, the receiver assembly 112 is typically acquired by a user in an assembled state. Furthermore, before the cradle 160 is assembled to the receiver 120, the collar 140 is first assembled to the receiver 120.

During assembly of the receiver assembly 112, the collar 140 is positioned within the base of the receiver 120 so that the outer convex surface 152 rests generally along the spherical cavity located within the base 126 of the receiver 120. The collar 140 is positioned within the receiver 120 such that the top surface 141 of the collar 140 is facing the top surface 128 of the receiver 120. Even when the collar 140 is in its circumferentially compressed state, the collar 140 cannot exit the receiver 120 through its central opening 137. Additionally, the pair of wings 147 protruding from the outer convex surface 152 of the collar 140 is generally mated with the pair of rounded pivot features 135 within the receiver. As mentioned above, the wings 147 mated with the pivot features 135 function to secure the positioning of the collar 140 and permit the collar 140 to articulate generally along a single plane relative to the receiver 120.

Once the collar 140 is assembled to the receiver 120, the cradle 160 can then be placed above the receiver 120 such that the bottom surface 26 of the cradle 160 is facing the top surface 28 of the receiver 120. The cradle 160 is then dropped into the center of the receiver 120 (between the arms 129) until the cradle 160 rests generally circumferentially within the round inner walls of the receiver 120 and the base 168 of the cradle 160 sits on the steps 138. The cradle 160 is then aligned (a tool may be engaged into the tool engaging features 161 to accomplish this) so that the first outer diameter notches 163 of the cradle 160 are aligned over the steps 138 of the receiver 120. This allows the cradle 160 to travel past the steps 138 towards the base 126 of the receiver 120 until the base 168 of the locking ledges 162 rest against the inside wall of the receiver 120 and prevent the cradle 160 from traveling further down towards the bottom surface 126 end of the receiver 120. At this point, the cradle 160 can be rotated along its central axis in the clockwise direction (again, a tool may be engaged into the tool engaging features 161 to accomplish this) so that the locking ledges 162 travel clockwise beneath the steps 138 of the receiver 120. The cradle 160 is rotated clockwise until the steps 138 are forced past the locking protuberances 190 of the cradle 160 and the steps 138 are situated within the second outer diameter notches 191. When the steps 138 of the receiver are situated within the second outer diameter notches 191, the cradle 160 is permanently secured into place and the receiver assembly 112 is generally complete (and best shown in FIG. 12).

The final step in assembling the spinal anchor assembly 100 during manufacturing and before being released for use is assembling the bone screw 111 to the receiver assembly 112. To accomplish this, a capture structure 116 of a bone screw 111 is generally concentrically aligned with the central opening 137 of a receiver. The capture structure 116 is then passed through the central opening 137 of the receiver 120, which has a larger diameter than the capture structure 116.

As the capture structure 116 passes through the central opening 137 it pushes against the bottom surface 149 of the collar 140 until the collar 140 is pushing up against the base 168 of the cradle 160. The capture structure 116 can then advance past the inner chamfer 46 of the collar 140 by forcing the collar 140 to increase circumferentially (by further lengthening the slot 144) until the largest diameter of the capture structure 116 passes through the inner protruding ring 151. Once the capture structure 116 passes through the inner protruding ring 151, the collar 140 begins to generally return to its original circumference and capture the capture structure 116 (best shown in FIG. 12). Proper orientation is ensured such that the interior protrusions 109 are mated with the flat surfaces 119 on the capture structure 116.

At this point, the connection between the bone screw 111 and receiver assembly 120 resembles a ball-and-socket joint, but with limited articulation to only along a single plane. More specifically, the capture structure 116 is free to articulate along a single plane relative to the collar 140 and the collar is able to articulate along a single plane relative to the receiver 120. Thus, the collar 140, bone screw 111 and receiver 120 are able to articulate relative to each other along a single plane until they are locked into position. By way of example, the bone screw is able to articulate and form an angle between its longitudinal axis and the longitudinal axis of the receiver 120 of approximately 30 degrees in either direction, for a total of 60 degrees of movement) in the articulating plane.

Therefore, a clinician may configure a spinal fixation system using at least one spinal anchor assembly 100, at least one additional bone screw assembly (i.e. fixed, provisionally locking, polyaxial), and at least one rod. The clinician is able to easily align the rod with the receiver assembly 112 of the spinal anchor assembly 100. Additionally, the clinician may leverage the uniplanar screw to direct a correcting force to the associated vertebra to correct positioning or alignment of the vertebra (e.g. derotation). Thereafter, the closure structure 13 can be engaged to press the rod against the cradle 160, which in turn presses the capture structure 116 against collar 140, and the collar 140 against the receiver 112. Ultimately, the frictional engagement between the closure structure 13, rod, cradle 160, capture structure 116, cradle 140, and cavity of the receiver 120 are such that the bone screw 111 and receiver assembly 112 are secured in a desired final position relative to each other.

FIGS. 19-30 illustrate an example of a spinal anchor assembly 200 according another embodiment of a uniplanar spinal anchor. The spinal anchor assembly 200 includes a bone screw 211, a receiver assembly 212, and a closure structure 13 (shown in FIGS. 5-7). The spinal anchor assembly 200 is preferably composed of a metal (e.g. titanium, stainless steel, etc.).

The bone screw 211 of the present invention is configured to securely engage within a bony structure (e.g. pedicle of a vertebra). The receiver assembly 212 is able to articulate relative to the bone screw 211 along a single plane. This uniplanar engagement between the receiver assembly 212 and the bone screw 211 permits some flexibility for positioning the rod, while still providing the ability to leverage the anchor assembly 200 to manipulate the vertebra to correct positioning and alignment of the vertebra. By way of example, the anchor assembly may be implanted such that the articulating plane is the sagittal plane (i.e. movement is cranial-caudal). Positioned as such, force may be applied to the screw in the transverse plane (i.e. medial/lateral direction) to derotate a vertebra.

Figure 21:
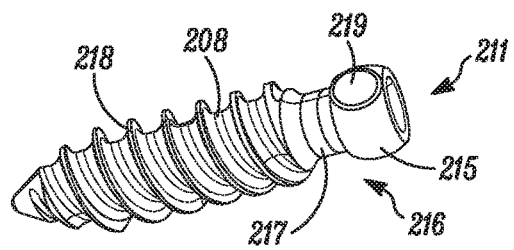
FIG. 21 is a perspective view of the bone screw forming part of an anchor assembly of FIG. 19.
Figure 22:
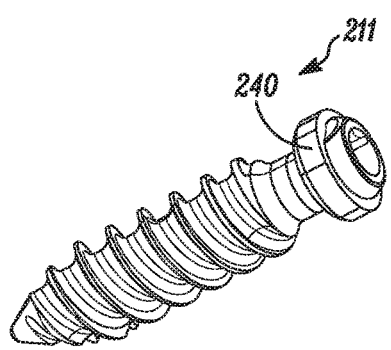
FIG. 22 is a perspective view of the bone screw of FIG. 21 forming part of an anchor assembly of FIG. 10.

FIG. 21 illustrates an example embodiment of the bone screw 211. The bone screw 211 of the spinal anchor assembly 200 is comprised of a shank 217, a body 208, and a capture structure 216. At least one helically-wound bone implantable thread 218 extends radially from the body 208 and functions to secure the placement of the bone screw 211 within a bony structure. Additionally, the capture structure 216 includes flat surfaces 219 on opposing sides of the capture structure 216. The flat surfaces 219 function to assist in restricting the rotation between the bone screw 211 and the collar 240 along its longitudinal axis, as will be discussed in more detail below. The capture structure 216 may comprise a screw head. The screw head may comprise opposing fifth and sixth sides and opposing seventh and eight sides.

The capture structure 216 includes at least one tool engaging feature that can be used, for example, to engage and attach various tooling for aligning and advancing the bone screw 211 into a bony structure. The generally spherically-shaped portions 215 of the capture structure 216 allow the capture structure 216, for example, to articulate within the collar 240 along a single plane. The surface of the capture structure 216 may be textured (e.g. scored or knurled) for enhancing frictional engagement with the collar 240, which assists in securing the position of the bone screw 211 relative to the receiver assembly 212, as will be discussed in more detail below.

Figure 19:
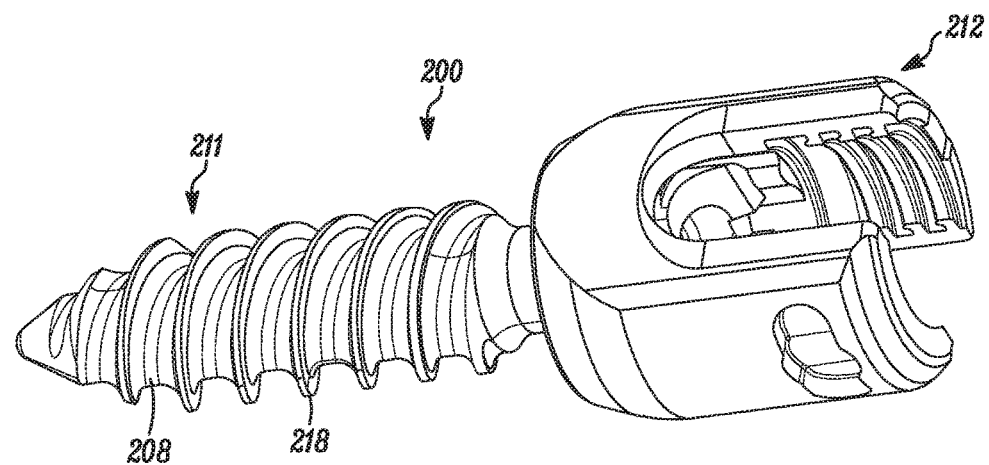
FIG. 19 is a perspective view of an another anchor assembly according to a third example embodiment.
Figure 20:
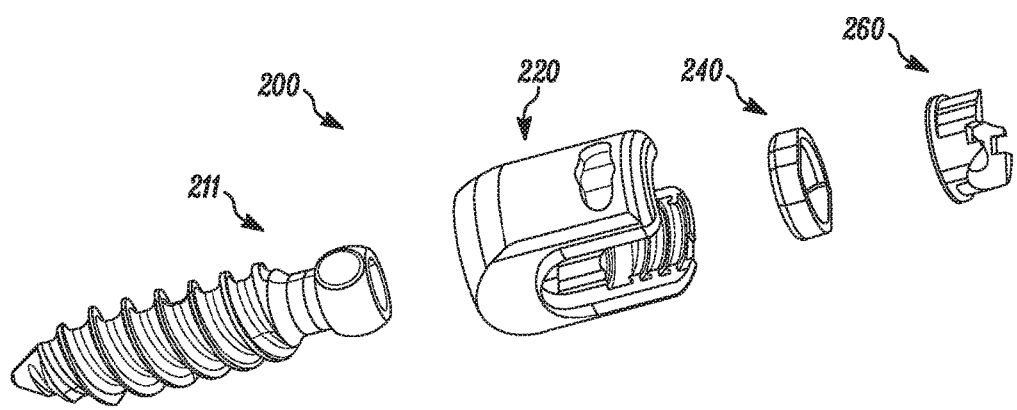
FIG. 20 is an exploded view of the anchor assembly of FIG. 19.
Figure 23:
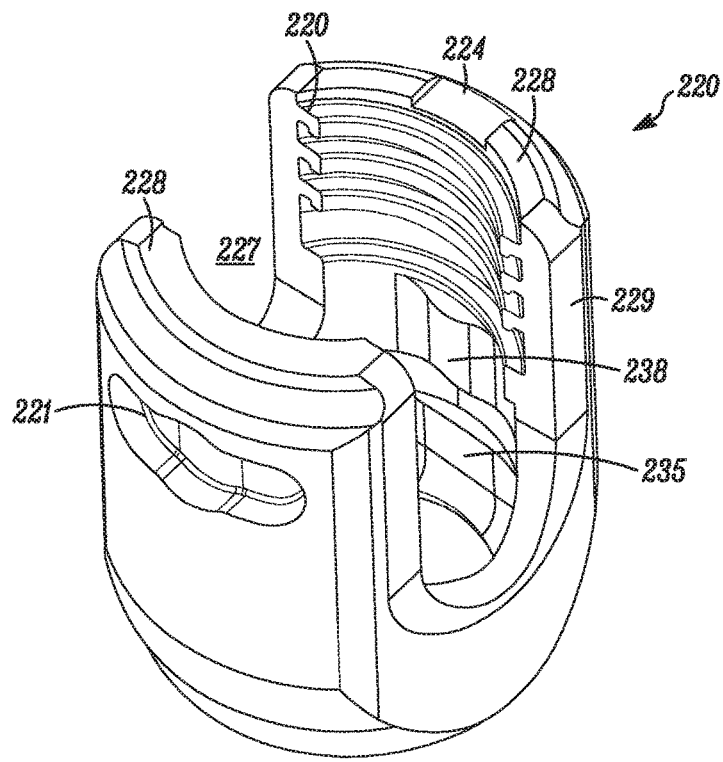
FIG. 23 is a perspective view of a receiver forming a part of the anchor assembly of FIG. 19.
Figure 24:
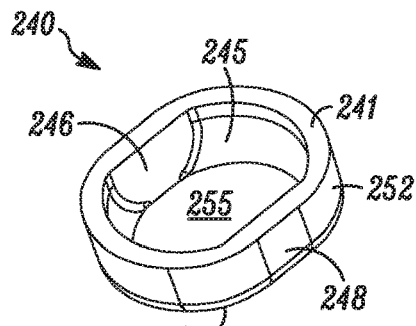
FIG. 24 is a perspective view of one example collar forming part of the anchor assembly of FIG. 19.
Figure 25:
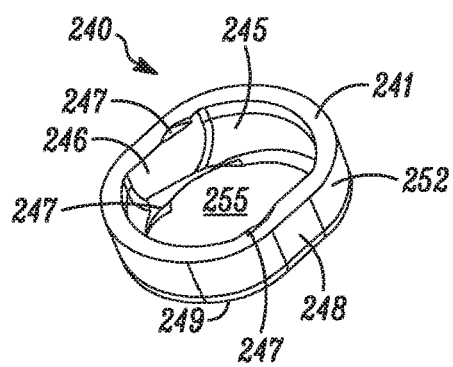
FIG. 25 is a perspective view of another example collar forming part of the anchor assembly of FIG. 19.
Figure 26:
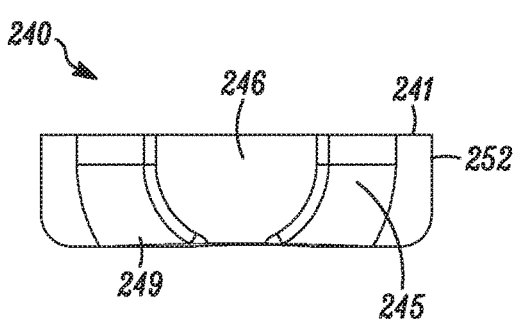
FIG. 26 is a partial cross section view of the collar of FIG. 24.
Figure 27:
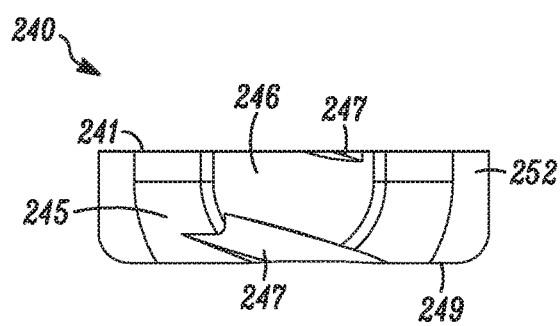
FIG. 27 is a partial cross section view of the collar of FIG. 25.
Figure 28:
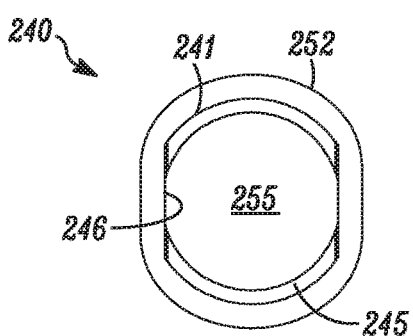
FIG. 28 is a top view of the collar of FIG. 24.
Figure 29:
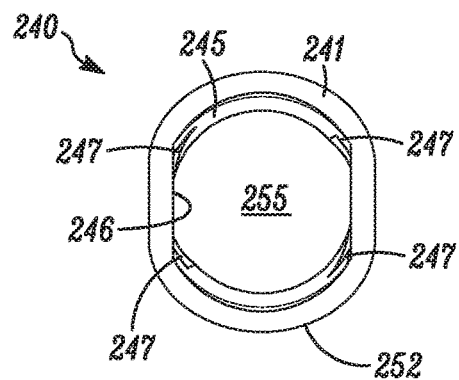
FIG. 29 is a top view of the collar of FIG. 25.
Figure 30:
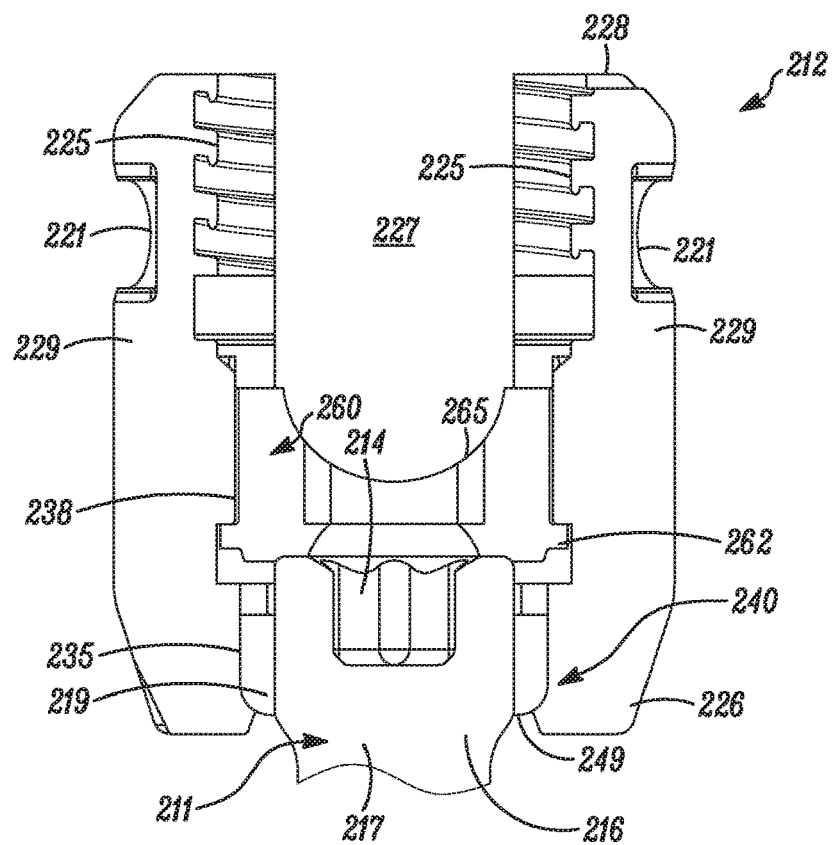
FIG. 30 is a partial cross section view of the anchor assembly of FIG. 19.

FIGS. 23 and 30 illustrate an example embodiment of a receiver assembly 212. The receiver assembly 212 is typically provided in an assembled state (as shown in FIG. 19) and includes a receiver 220, a retaining and articulating structure or collar 240, and a cradle 260. The receiver 220 has a generally U-shaped appearance with a generally cylindrical inner profile and a faceted outer profile. A base 226, with a pair of upstanding arms 229 forms a U-shaped cradle which define U-shaped openings 227 through the faceted sides of the receiver 220. It will be appreciated however, that receiver 220 may be provided having side openings selected from variety of suitable shapes and dimensions depending, in part, on the size and shape of the rod to be received.

Both arms 229 have at least one helical wound guide and advancement structure 225 at least partially situated along their internal walls beginning from the top surface 228 end of the receiver 220. The guide and advancement structure 225 of the receiver 220 are configured to mate with at least one exterior helically-wound guide and advancement structure of a closure structure (not shown in this embodiment), which assist in preventing the arms from spreading open. The closure structure 13 described in the first embodiment may be used with this second embodiment of the present invention to achieve the securing of at least a portion of a rod within a receiver assembly 212. Moreover, any variation of closure structures may be used to secure at least a portion of a rod within the receiver assembly 212, without departing from the scope of this invention.

The outer surface of the receiver 220 includes tooling attachment features, such as grip bores 221, on the outer surface of both arms 229. Grip bores 221 function, for example, to allow a variety of tools to engage the receiver assembly 212 for subsequent implantation and positioning of the receiver assembly 212 and screw assembly 200. Additional features of the receiver 220 include two steps 238 extending inwardly from the inside walls of the arms 229 (with one step 238 situated on each arm 229). By way of example only, each step 238 spans at least a portion of the inside wall of an arm 229 and are positioned generally 180 degrees apart from each other. Located within the base 126 end of the receiver 120 is a cavity that is defined by a generally spherical surface and is sized and shaped for slidable mating and eventual frictional engagement with collar 240, as described below. Along the walls of the cavity within the base 226 of the receiver is a pair of rounded features 235. The rounded features 235 are located approximately 180 degrees apart from each other and function to secure the positioning of the collar 240.

FIGS. 24-29 illustrate example embodiments of a retaining and articulating structure or collar 240. The collar 240 is comprised of a top surface 241, a bottom surface 249, an outer convex surface 252, an inner concave surface 245, an interior faceted surface 246, and an exterior faceted surface 248. An embodiment of the collar 240 shown in FIGS. 24, 26, and 28 comprises a first side and a second side opposing the first side, wherein the first side and the second side are straight and parallel to each other, said collar having a third side and a fourth side opposing said third side, wherein the third side and the fourth side are rounded, and wherein the four sides define an inner cavity. In some embodiments of the collar 240, interior surfaces of said opposing third side and fourth side are spherical.

In its preferred embodiment, the bone screw 211 may be assembled to the receiver assembly 212 by passing the distal end of the bone screw through the top opening of the receiver 212 and collar 240 (and before the cradle is assembled to the receiver 220) until the capture structure 216 is resting in the collar 240 (which is resting in the base of the receiver 220) forming collar assembly 280. In one embodiment of collar 240, the inner concave surfaces 245 has helical recesses 247 shaped into said inner concave surface 245. Helical recesses 247 facilitate the placement of the bone screw 211 through the aperture 255 of the collar 240. By way of example, helical recesses 247 allow for screws whose advancement structure 218 have diameters larger than aperture 255 to be used in bone screw assembly 200. The helical thread 218 of a large diameter bone screw is threaded through helical recesses 247 until shank 217 has passed through the aperture 255 of collar 240. Proper orientation is ensured such that the interior faceted surface 246 are mated with the flat surfaces 219 on the capture structure 216.

Exterior faceted surfaces 248 are situated on opposing sides of the outer convex surface 252 of the collar 240. Exterior faceted surface 248 is sized and shaped to mate with the rounded feature 235 of the receiver 220. By way of example, the exterior faceted surfaces 248 may be D-shaped, but may be any size and shape suitable for limiting the movement of the collar 240 (and associated bone screw 211). When mated, the exterior faceted surface 248 assist in positioning the collar 240 within the receiver 220. The bone screw 211 is able to pivot relative to the receiver 220 along a single plane for subsequent secure positioning and implantation, as described above and will be described in more detail below. Interior faceted surfaces 246 situated inwardly on opposing sides of the inner concave surface 245 of the collar 240. By way of example, the interior faceted surfaces 246 may be D-shaped, but may be any size and shape suitable for directing and limiting the pivot direction of the capture structure 216 (and associated bone screw 211). In those embodiments in which the interior faceted surface 246 is D-shaped, it may include a straight edge portion and a curved portion forming the "D." The interior faceted surfaces 246 function to mate with the flat surfaces 219 on a capture structure 216 to prevent the rotation of a bone screw 211 relative to the collar 240 along their longitudinal axis.

Furthermore, the cradle 260 in the present embodiment is generally identical in feature and function as the cradle 60 described in the second embodiment, and thus will not be repeated in detail again here.

At this point, the connection between the bone screw 211 and receiver assembly 220 resembles a ball-and-socket joint, but with limited articulation in only a single plane. More specifically, the capture structure 216 is free to articulate along a single plane relative to the collar 240. The collar 240, bone screw 211 and receiver 220 are able to articulate relative to each other along a single plane until they are locked into position, as will be described in detail below. By way of example, the bone screw is able to articulate and form an angle between its longitudinal axis and the longitudinal axis of the receiver 220 of approximately 30 degrees in either direction, for a total of 60 degrees, along the single articulating plane.

Therefore, a clinician may configure a spinal fixation system using at least one spinal anchor assembly 200, at least one additional bone screw assembly of any variety of constraints (e.g. fixed, provisionally locking, polyaxial), and at least one rod. The clinician is able to easily align the rod with the receiver assembly 212 of the spinal anchor assembly 200. Additionally, the clinician may leverage the uniplanar screw to direct a correcting force to the associated vertebra to correct positioning or alignment of the vertebra (e.g. derotation). Thereafter, the closure structure 13 can be engaged to press the rod against the cradle 160, which in turn presses the capture structure 216 against collar 240, and the collar 240 against the receiver 212. Ultimately, the frictional engagement between the closure structure 13, rod, cradle 260, capture structure 216, collar 240, and cavity of the receiver 220 are such that the bone screw 111 and receiver assembly 112 are secured in a desired final position relative to each other.

Figure 31:
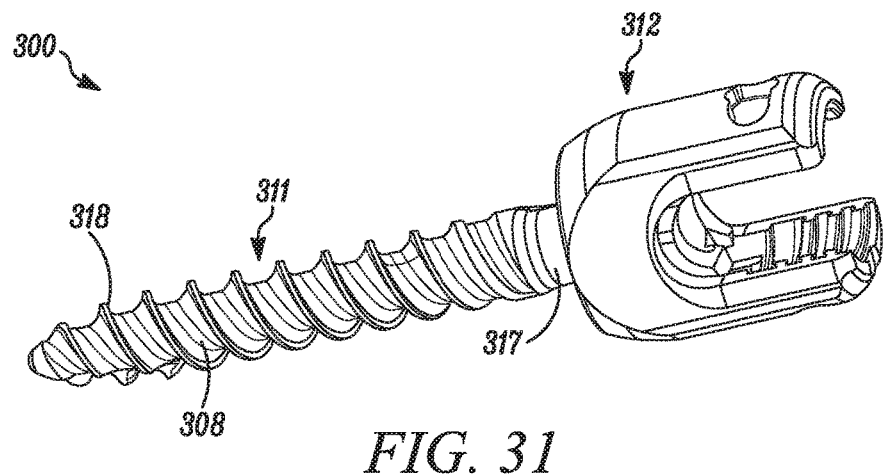
FIG. 31 is a perspective view of another spinal anchor assembly, according to a fourth example embodiment.
Figure 32:
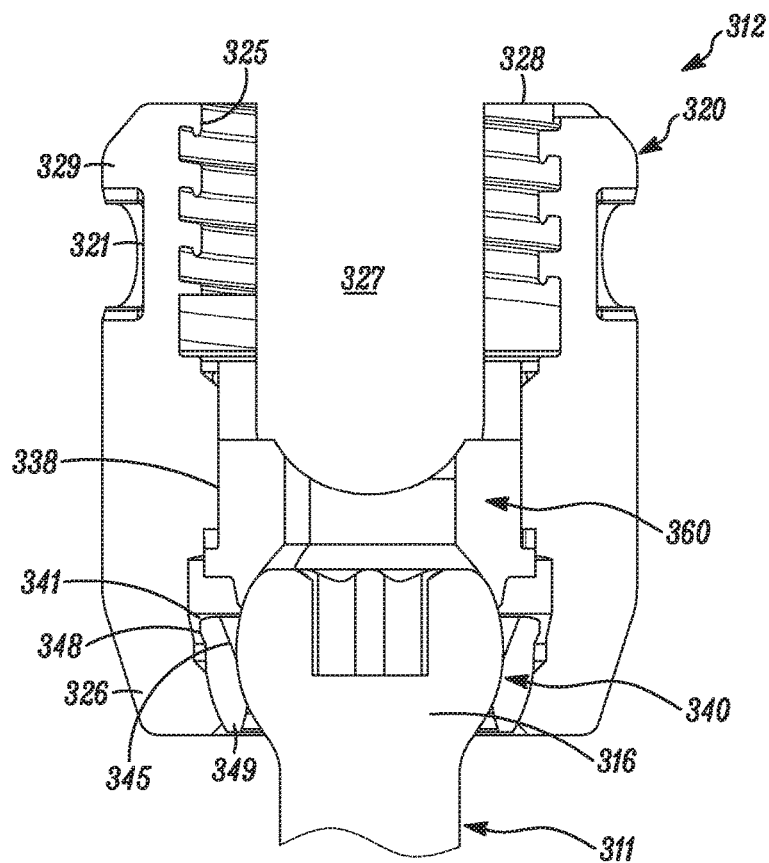
FIG. 32 is a partial cross section view of the spinal anchor assembly of FIG. 31.

FIGS. 31 and 32 illustrate an example of a spinal anchor assembly 300 according to another embodiment of the present invention. The spinal anchor assembly 300 includes a bone screw 311, and a receiver assembly 312. The spinal anchor assembly 300 is preferably composed of a metal (e.g. titanium, stainless steel, etc.). The spinal anchor assembly 300 may be available to a clinician in a pre-assembled state such that the receiver assembly 312 is jointly attached to the capture structure 316 of the bone screw 311 and has full polyaxial motion. That is, the receiver assembly 312 and bone screw 311 are able to articulate in all directions and can ultimately be secured at any number of angles relative to each other and in any directions.

When the desired angular orientation is achieved to facilitate rod capture and the rod is received therein, the receiver assembly 312 is locked into position relative to the bone screw 311. For this to occur, a closure structure 13 is engaged and presses down on the rod which presses down on the cradle 360 which presses down on the capture structure 316. The capture structure presses down on the collet 340 and collet in turn presses into the receiver 320 which compresses the slot 344 and causes the inner spherical surface 349 to frictionally engage and secure the capture structure 316. This permanently fixes the orientation of the receiver 320 relative to the bone screw 311.

The bone screw 311 of the present invention is configured to attach securely within a bony structure (e.g. pedicle of a vertebra) with the receiver assembly 312 assembled to the capture structure 316 of the bone screw 311. The receiver assembly and bone screw 311 are configured to engage in with full polyaxial motion. This polyaxial engagement between the receiver assembly 312 and bone screw 311 provides for simplified positioning and rod placement. The receiver assembly 312 is configured to receive a rod and a closure structure 13 secures the rod within the receiver assembly 312. Once the rod is positioned in the receiver assembly 312 a closure structure 13 will lock the rod in the receiver assembly 312, which also inhibits additional movement between the receiver assembly 312 and the bone screw 311.

The bone screw 311 of the spinal anchor assembly 300 is comprised of a shank 317, a body 308, and a capture structure 316. At least one helically-wound bone implantable thread 318 extends radially from the body 308 and functions to secure the placement of the bone screw 311 within a bony structure. The generally spherical shape of the capture structure 316 allows it, for example, to ultimately be frictionally engaged with the generally spherical features within the receiver assembly 312. The surface of the capture structure 316 may be textured (e.g. scored or knurled) for enhancing frictional engagement with the retaining and articulating structure or collar 340.

The receiver assembly 312 is typically provided in an assembled state and includes a receiver 320, a retaining and articulating structure or collar 340, and a cradle 360. The receiver 320 has a generally U-shaped appearance with a generally cylindrical inner profile and a faceted outer profile. A base 326, with a pair of upstanding arms 329 form a U-shaped cradle which define U-shaped openings 327 through the faceted sides of the receiver 320. It should be appreciated that side openings in the receiver may be provided in a variety of suitable shapes and dimensions depending on the size and shape of the rod to be received.

Both arms 329 have at least one helically-wound guide and advancement structure 325 at least partially situated along their internal walls beginning from the top surface 328 end of the receiver 320. The guide and advancement structure 325 of the receiver 320 are configured to mate with at least one exterior helically wound guide and advancement structure 72 of the closure structure 13. Although an embodiment of a closure structure is described in detail herein, any number of closure structures may be used without departing from the scope of this invention. When the internal and external guide and advancement structures 325, 72 of the closure structure 13 and receiver 320 are interlocked, their connection prevents the arms 329 of the receiver 320 from spreading open due to the mating features of the guide and advancement structures 325 and 72. This interlocked configuration prevents splaying of the arms 329.

The outer surface of the receiver 320 includes tooling attachment features, such as grip bores 321 on the outer surface of both arms 329. These tooling attachment features function, for example, to allow a variety of tools to engage the receiver assembly 312. Additional features of the receiver 320 include two steps 338 extending inwardly from the inside walls of the arms 329 (with one step 338 situated on each arm 329). By way of example only, each step 338 spans at least a portion of the inside wall of an arm 329 and are positioned generally 180 degrees apart from each other. Located within the base 326 end of the receiver 320 is a cavity that is defined by a generally spherical surface which is sized and shaped for slidable mating and eventual frictional engagement with the retaining and articulating structure or collar 340, as described below.

The collar 340 is comprised of a top surface 341, a bottom surface 349, an outer convex surface 352, an inner concave surface 345, and a radial protrusion 348. Notably, the collar 340 is not continuous, and instead includes a slot (similar to the slot 44 discussed and illustrated in the second embodiment of the spinal anchor assembly 300) extending from the top surface 341 to bottom 342. The slot is dimensioned to be a distance X and allows the collar 340 to be temporarily expanded or compressed to receive the capture structure 316 and to secure the collar 340 around the capture structure 316, similar to the collar 40 described above, and thus will not be repeated in detail again here. Furthermore, the cradle 360 in the present embodiment is generally identical in feature and function as the cradle 60 described in the second embodiment, and thus will not be repeated in detail again here.

As discussed above, the connection between the bone screw 311 and receiver assembly 320 resembles a ball-and-socket joint before being locked into a configuration. This ball-and-socket characteristic enables the receiver assembly 320 to accommodate and capture a rod by rotating to achieve various angular positions relative to the fixed bone screw 311. Therefore, as a clinician configures a spinal fixation system using at least one polyaxial bone screw assembly 300, at least one additional bone screw assembly (i.e. fixed, provisional locking, polyaxial), and at least one rod, the clinician is able to easily align the rod with the receiver assembly 312 of the spinal anchor assembly 300. The steps for locking in place of the spinal anchor assembly 300 in a desired position, in addition to the locking of the spinal anchor assembly 300 with the rod(s) are generally the same as the steps detailed in the second embodiment of the spinal anchor assembly 200, and thus will not be repeated here.

Figure 33:
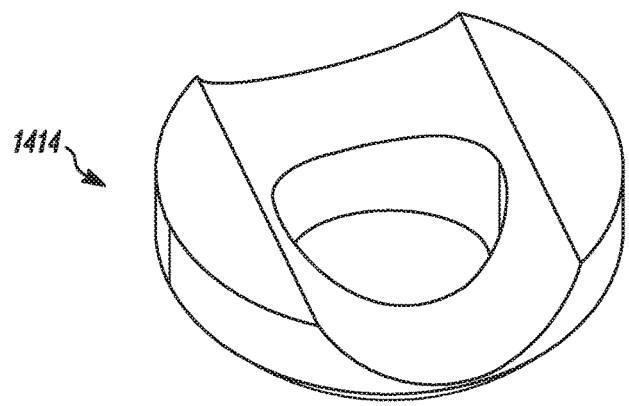
FIG. 33 is a partial cross section view of the spinal anchor assembly in an unlocked position, according to a fifth embodiment of the present invention.
Figure 34:
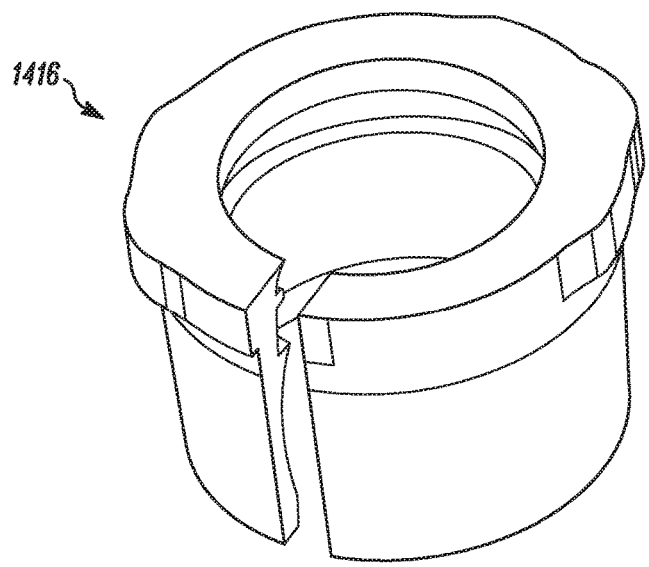
FIG. 34 is a partial cross section view of the spinal anchor assembly of FIG. 33 in the locked position.

FIGS. 33-36 illustrate an example of a spinal anchor assembly 1400 according to another embodiment of a provisional locking assembly. The spinal anchor assembly 1400 includes a bone screw 1410 and a receiver assembly 1412 similar in functions and features to the embodiment of the spinal anchor assembly 10 disclosed herein. Like features and functions will not be repeated. The spinal anchor assembly 1400 differs from the spinal anchor assembly 10 in that it includes a load ring 1414 engaged with the collet 1416 (FIGS. 33-34).

Figure 35:
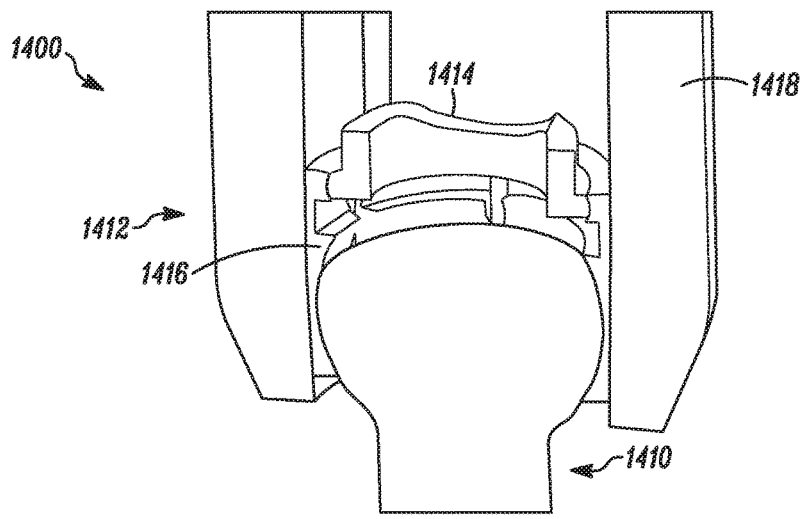
FIG. 35 is a perspective view of the loading ring of FIG. 33.
Figure 36:
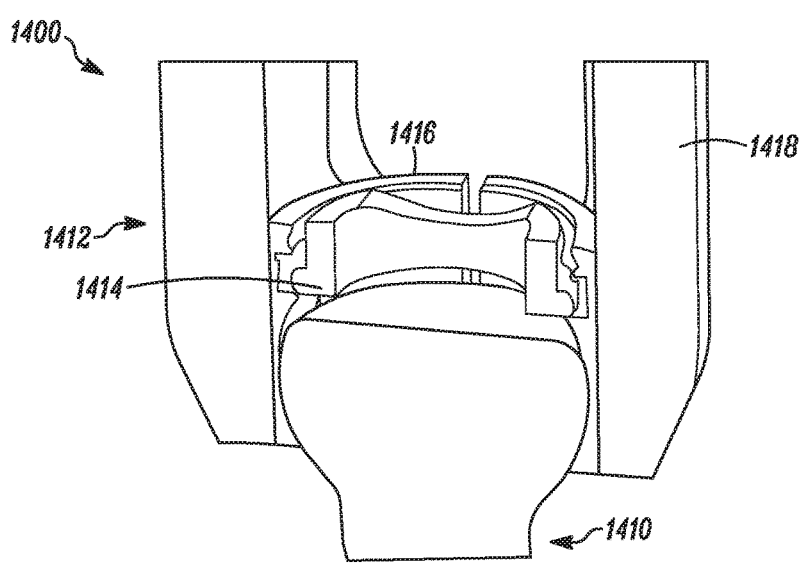
FIG. 36 is a perspective view of the collet of FIG. 33.
Figure 37:
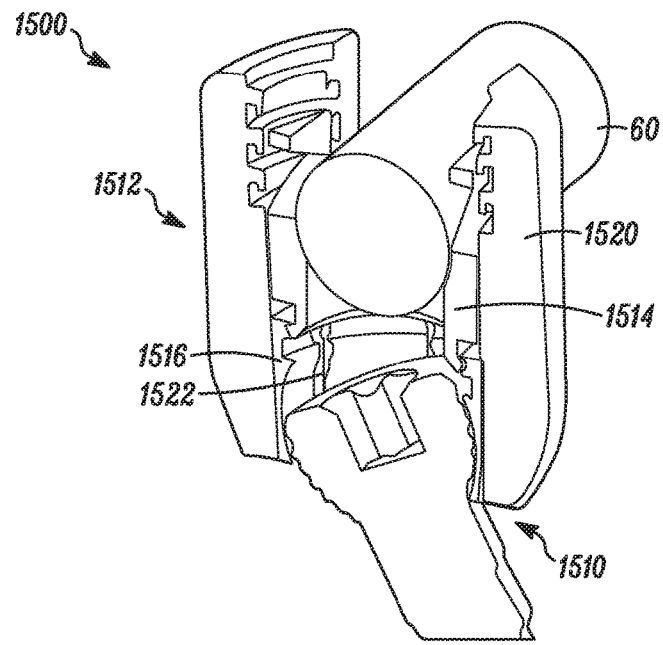
FIG. 37 is a partial cross section view of a spinal anchor assembly in an unlocked position according to the sixth embodiment of the present invention.
Figure 38:
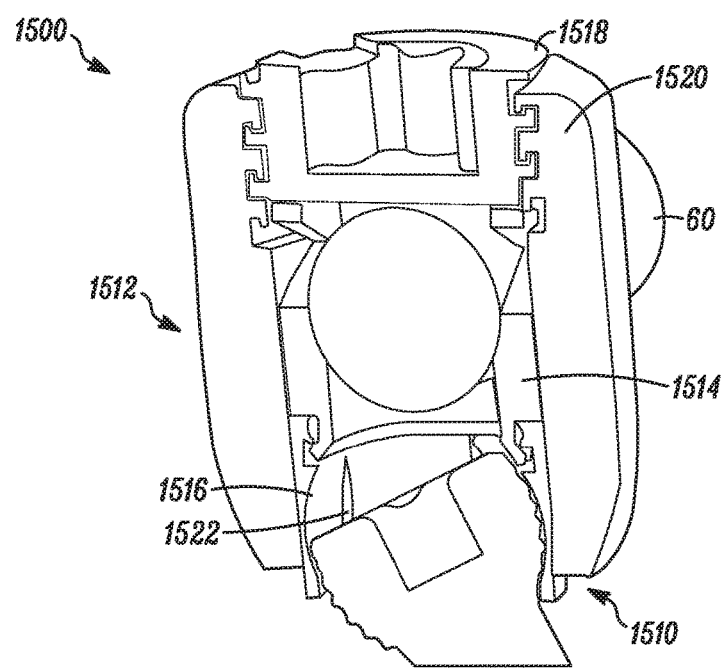
FIG. 38 is a partial cross section view of the spinal anchor assembly of FIG. 37 in the locked position.

As shown in FIG. 35, the load ring 1412 snaps into the collet 1416 and prevents the collet 1416 from compressing on the bone screw 1410 and or capture structure 13. This allows the polyaxial motion of the bone screw 1410 relative to the receiver assembly 1412 to be maintained even after reduction of the collet 1416 into the receiver 1418. Thus, the collet 1416 can become securely engaged (or wedged) into the receiver 1418 while the bone screw 1410 is able to still articulate within the collet 1416 to provide full polyaxial motion between the bone screw 1410 and receiver assembly 1412.

When sufficient force is applied onto the load ring 1414, the load ring 1414 disengages from the collet 1416 (as shown in FIG. 35), thus enabling the collet 1416 to securely engage the capture structure 1420 of the bone screw 1410, which inhibits additional movement between the receiver assembly 1412 and the bone screw 1411.

Figure 39:
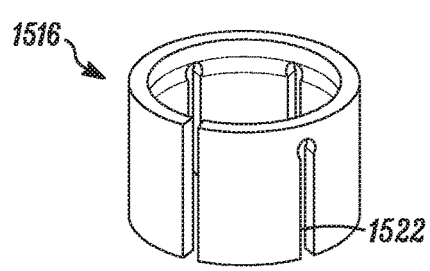
FIG. 39 is a perspective view of the split ring of FIG. 37.
Figure 40:
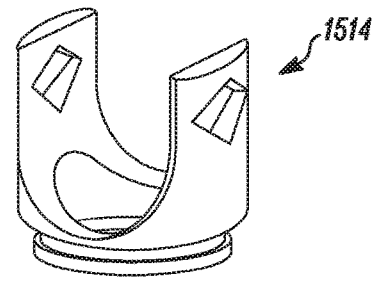
FIG. 40 is a perspective view of the loading ring of FIG. 37.

FIGS. 37-40 illustrate an example of a spinal anchor assembly 1500 according still another embodiment of invention provisional locking assembly. The spinal anchor assembly 1500 includes a bone screw 1510 and a receiver assembly 1512 similar in functions and features to the embodiment of the spinal anchor assembly 1410. Like features and functions will not be repeated here. The spinal anchor assembly 1500 differs from the spinal anchor assembly 10 in that it includes a load ring 1514 and a split ring 1516 (as shown in FIGS. 39-40).

The loading ring 1514 snaps into the split ring 1516 and prevents the split ring 1516 from compressing on the bone screw 1510 and/or capture structure 1518 of the bone screw 1510. This allows the polyaxial motion of the bone screw 1510 relative to the receiver assembly 1512 to be maintained even after reduction of the split ring 1516 into the receiver 1520. Thus, the split ring 1516 can become securely engaged (or wedged) into the receiver 1520 while the bone screw 1510 is able to still articulate within the split ring 1516.

To lock the receiver assembly 1512 relative to the bone screw 1511, additional force is applied by engaging a capture structure 1518 (or lock screw) into the receiver assembly 1512. As the capture structure 1518 is further engaged into the receiver 1514, the bottom surface 71 of the closure structure 1518 is forced down upon the spring elements 1522 of the loading ring 1514 (best shown in FIGS. 37-38). As the spring elements 1522 compress, they apply increasing force onto the split ring 1516, thus permanently fixing the position of the bone screw 1510 relative to the receiver assembly 1512. Furthermore, the bottom surface 71 of the capture structure 13 forces down upon the captured rod. Ultimately, the rod 60, receiver assembly 1512, and bone screw 1510 will be finally fixed relative to each other.

Figure 41:
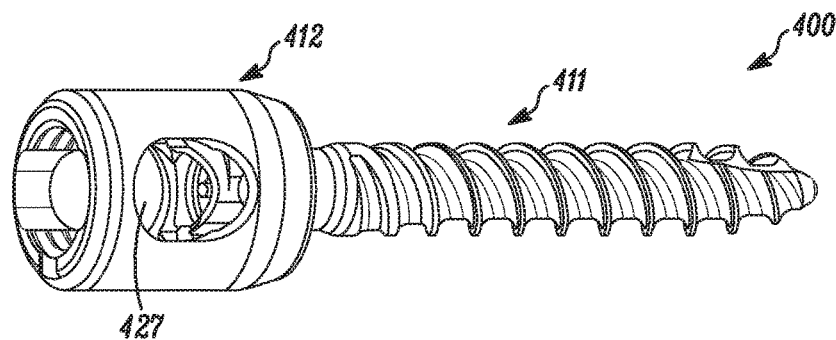
FIG. 41 is a perspective view of one example of a spinal anchor assembly, according to a seventh embodiment of the present invention.
Figure 42:
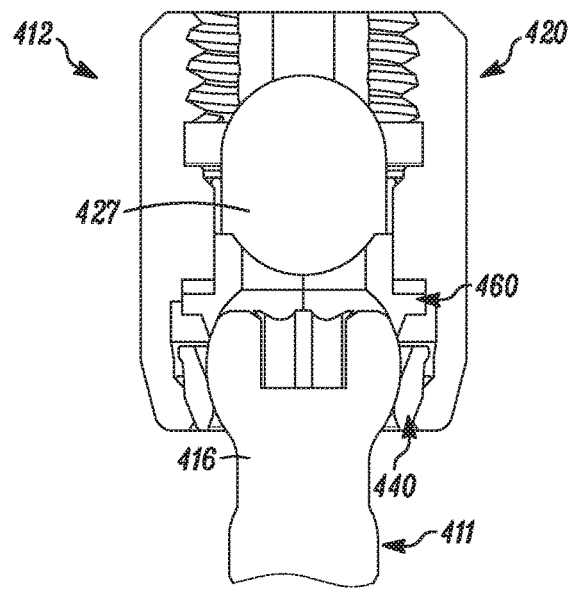
FIG. 42 is a partial cross section view of the spinal anchor assembly of FIG. 41.
Figure 43:
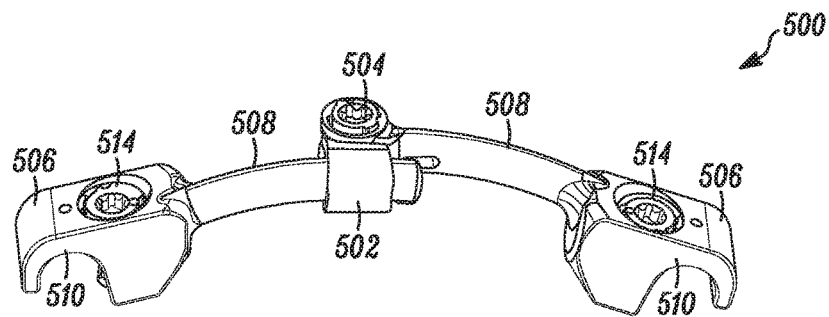
FIG. 43 is a perspective view of one an arched transverse connector according to one example embodiment.
Figure 44:
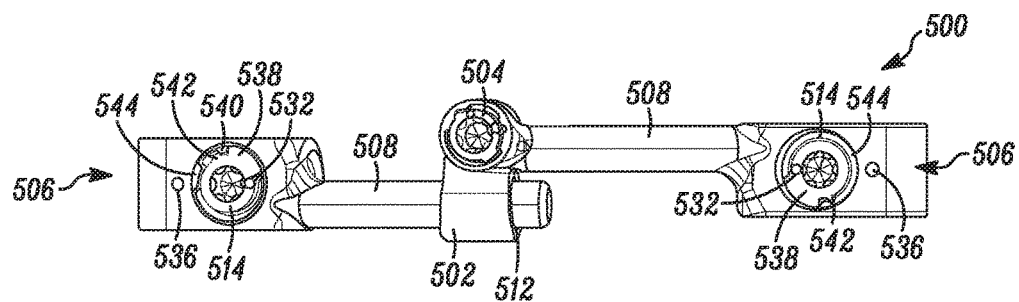
FIG. 44 is a top view of an arched transverse connector of FIG. 43.
Figure 45:
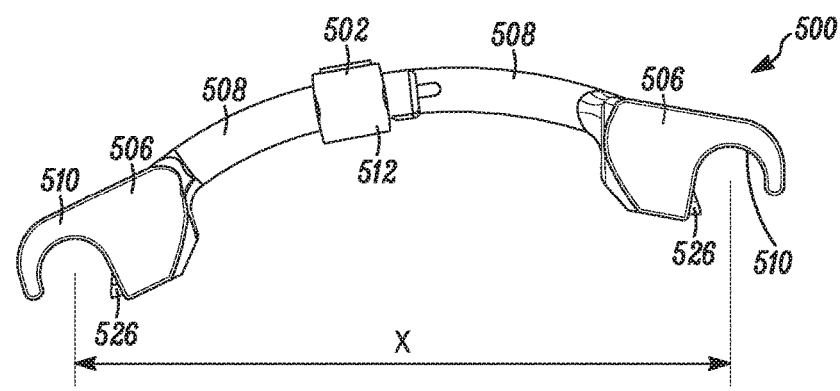
FIG. 45 is a side view of an arched transverse connector of FIG. 43.

FIGS. 41 and 42 illustrate an example of a spinal anchor assembly 400 according to a seventh embodiment. The spinal anchor assembly 400 includes a bone screw 411, a receiver assembly 412 having a collar 440 and a cradle 460. The spinal anchor assembly 400 is largely similar to the spinal anchor assembly 300 and like features will not be further described herein. The spinal anchor assembly 400 differs from the spinal anchor assembly 300 in that it includes a close-topped receiver assembly 412. The close topped receiver assembly 412 includes circular openings 427 to receive the rod. The rods slide through the circular shaped openings 427 and are locked with a closure structure. Any number of closure structures (including the closure structure 13 described herein) may be engaged into the receiver assembly 412 to secure the rod. Because the receiver assembly 412 is closed, the closure member may preferably be void of anti-splay features.

Figure 72:
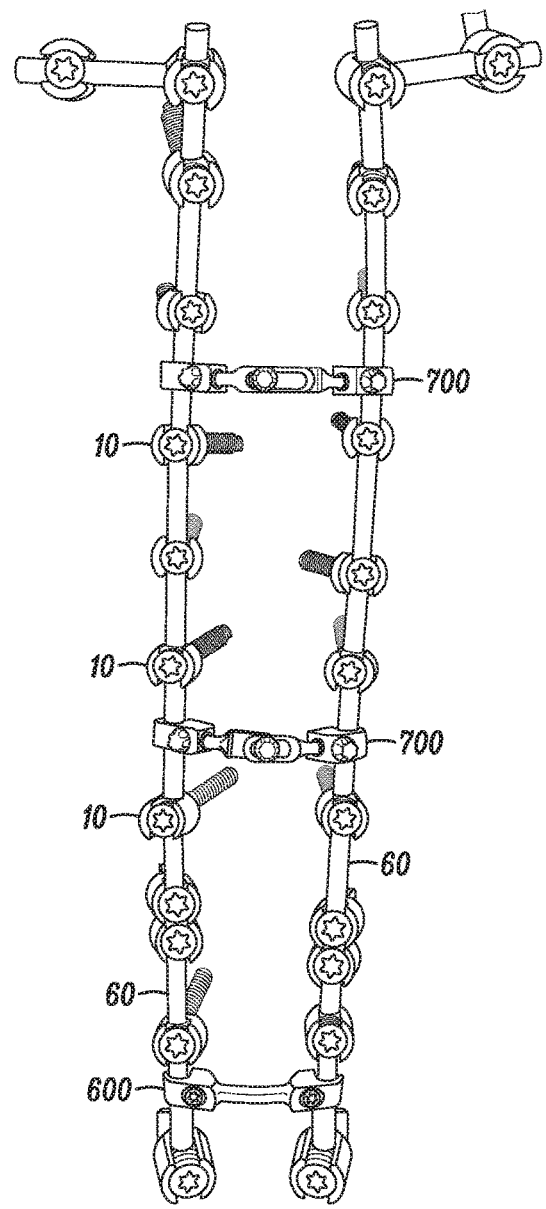
FIG. 72 is an exemplary configuration of a deformity spinal fixation assembly.

FIGS. 43-48 illustrate an example of an arched transverse connector 500 according to one example embodiment. The arched transverse connector 500 connects two rods that form a part of a spinal fixation assembly (for an example, refer to FIG. 72) situated on either side of the spinal column. The arched transverse connector 500 includes a cross joint 502 with an eccentric pin 504, and a pair of connector heads 506 located at the distal ends of connector arms 508. The eccentric pin 504 in the cross joint 502 enables a user to simply lengthen and shorten the distance between the arched recesses 510 along the tubular joint collar 512. Rotation of the eccentric pin 504 locks and unlocks the cross joint 502 to prohibit or allow translation of one connector arm relative to the other.

The transverse connector 500 is generally arched (as best viewed in FIGS. 43 and 45) with the cross connector arms 508 following a radial arc. The generally arched shape of the transverse connector 500 avoids any unnecessary dural impingement when the arched transverse connector 500 is implanted. This is particularly important when the arched transverse connector 500 is assembled to a posterior spinal fixation assembly. By way of example only, the distance between the center of the arched recesses 510 may range approximately between 25-100 mm (and shown as dimension X in FIG. 45). Preferably, the arched transverse connector 500 is composed of a metal (e.g. titanium, stainless steel, etc.), but may also be of a polymer (e.g. poly-ether-ether-ketone (PEEK)) or any other material suitable for the applications of the present invention. Additionally, the arched transverse connector 500 may be composed of a combination of both metal and polymer materials.

Each connector head 506 includes an eccentric pin 514 that is retained within a cavity 516 of the housing by a retaining c-ring 518. The cavity 516 extends generally perpendicular from the front surface 520 of the connector head 506 to at least partially through the connector head 506. The retaining c-ring 518 engages the circumferential step 522 on the outer surface of the eccentric pin 514 and the annular step 524 within the cavity 516, which restricts longitudinal movement of the eccentric pin 514 relative to the cavity 516. The engagement of the retaining c-ring 520 allows rotational movement of the eccentric pin 524 relative to the cavity 526. A connector head 506 includes an arched recess 520 that is shaped and dimensioned to allow the secure placement of a rod (e.g. rod). By way of example, rotation of the eccentric pin 514 secures a portion of a rod within an arched recess, as will be described in greater detail below.

The surfaces within the arched recesses 510 provide frictional engagement to a rod when eccentric pins 514 engage the rod along their engagement surfaces 526. Furthermore, the engagement surface 526 of the eccentric pins 514 and/or the surfaces within the arched recesses 510 may have surface features, or surface roughening, to enhance the frictional engagement between the arched transverse connector 500 and rods for enhanced security. By way of example, the eccentric pin 514 is shown as having a generally annular concavity to its engagement surface 526 (and best shown in FIG. 48). The generally annular concavity allows for a greater surface area contact between the eccentric pin 514 and a generally cylindrical shaped rod. However, the engagement surface 526 of an eccentric pin 514 may be provided in a variety of shapes and dimensions necessary for providing optimal contact between a variety of shaped and sized rods, without departing from the scope of this invention. For example, pin 504 may be threadably received through an end of the connector arm 508, such that as it is threaded into the connector arm, it squeezes the cross joint 502 to prohibit translation of the cross arms.

An eccentric pin 514 includes a top surface 528, a bottom surface 530, an engagement surface 526 and a positioning indicator 532. A tooling engaging feature 534 is centrally positioned along the top surface 528, which enables a variety of tools to engage the eccentric pin 514 and rotate it along its longitudinal axis (labeled as axis Y in FIG. 48). At least one positioning indicator 532 indicates to the user the relative rotational positioning of the eccentric pin 514 relative to the connector head 506. Additionally, at least one positioning indicator 536 may be on the front surface 520 of the connector head 506 to further assist the user in properly aligning the eccentric pin 514 relative to the connector head 506, for example, to securely engage a rod. By way of example, if the user aligns the positioning indicators 532, 536 of the eccentric pin and the connector head 506 adjacent to each other, the eccentric pin 514 will be in the appropriate rotational position relative to the connector head 506 to securely engage an rod within the adjacent arched recess 510. By way of further example, if the user rotates the eccentric pin 514 approximately 180 degrees from the previously described position (such that the positioning indicators 532 and 536 are aligned but not adjacent to each other), the eccentric pin 512 will be in the appropriate rotational position relative to the connector head 506 to release or accept an rod within the adjacent arched recess 510.

Figure 46:
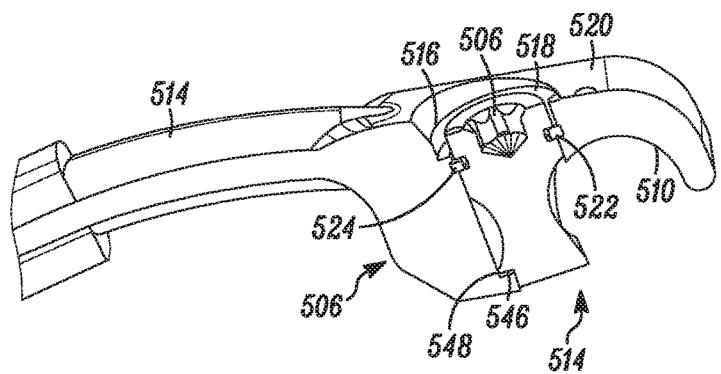
FIG. 46 is a partial section view of an arched transverse connector of FIG. 43.
Figure 47:
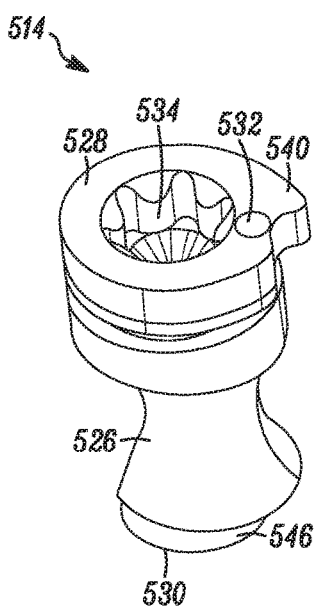
FIG. 47 is a perspective view of an eccentric pin of the arched transverse connector of FIG. 43.
Figure 48:
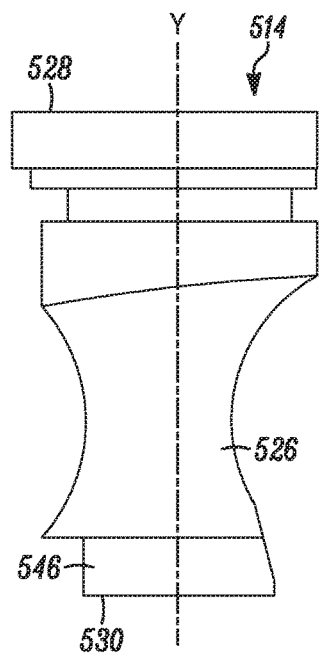
FIG. 48 is a side view of an eccentric pin of the arched transverse connector of FIG. 43.

FIGS. 46-48 further illustrate the eccentric pin 514, which includes a positional stop 538 and a locking protuberance 540 that radially extend out along a portion of the circumference of the top surface 528. The locking protuberance 540 locks the rotational positioning of the eccentric pin 514 once the locking protuberance 540 has passed a head notch 542 (and best shown in FIG. 44). This helps prevent the eccentric pin 514 from unfavorably rotating and releasing the rod from the associated arched recess 510. The positional stop 538 functions to limit the rotation of the eccentric pin 514 when the positional stop 538 comes into contact with the bumper 544.

Furthermore, the eccentric pin 514 includes an annular recess 546 centrally located along the longitudinal axis (Y) and adjacent the bottom surface 530 of the eccentric pin 514. The annular recess 546 functions to support the positioning of the bottom end of the eccentric pin 516 against the ledge 548 of the connector head 506. Specifically, since the eccentric pin 506 is generally eccentric, the annular recess 546 is a non-eccentric feature which maintains the alignment of the eccentric pin 514 within the connector head 506. Upon rotation of the eccentric pin 514 along its central axis within the connector head 506, the eccentric body of the pin acts as a cam and forces the protruding side of the eccentric pin 515 (relative to its longitudinal axis Y) against an rod captured in the associated arched recess 510.

Assembly of the arched transverse connector 500 to a pair of rods (i.e. rods) begins with a section of a first rod being captured within an unlocked first arched recess 510 and then a section of a second rod is captured within an unlocked second arched recess 510. The arched transverse connector 500 is then operated by rotating the eccentric pins 514 into their locked positions to permanently secure the rods as described above.

Figure 49:
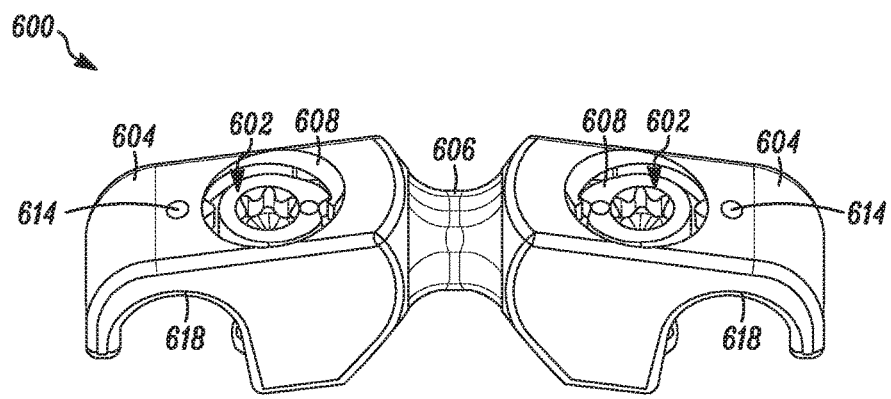
FIG. 49 is a perspective view of an arched transverse connector according to a second example embodiment.
Figure 50:
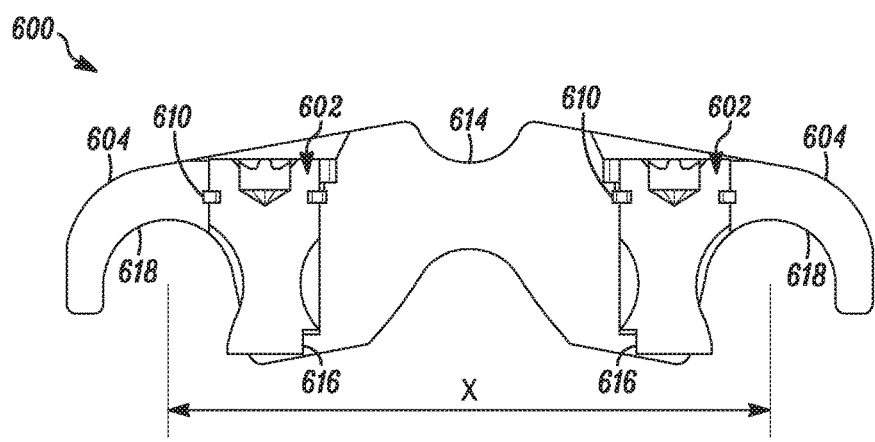
FIG. 50 is a cross section view of the arched transverse connector of FIG. 49.
Figure 51:
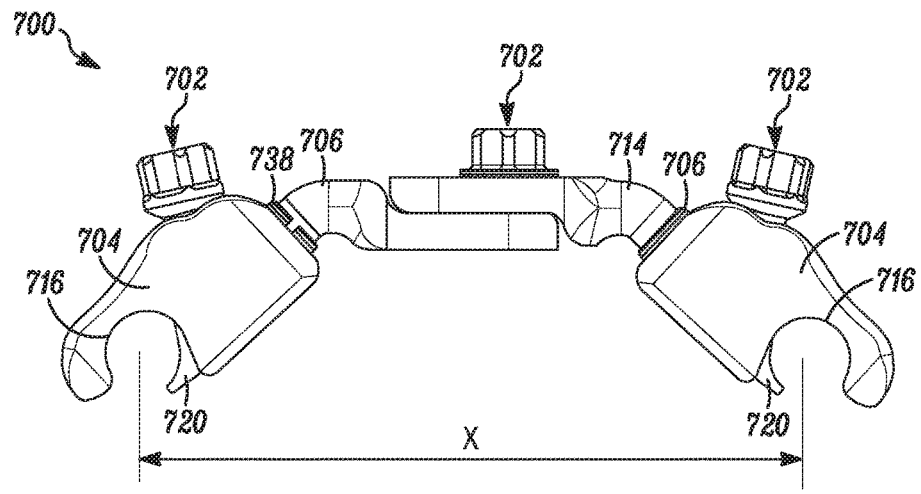
FIG. 51 is a side view of an arched transverse connector according to a third example embodiment of the present invention.
Figure 52:
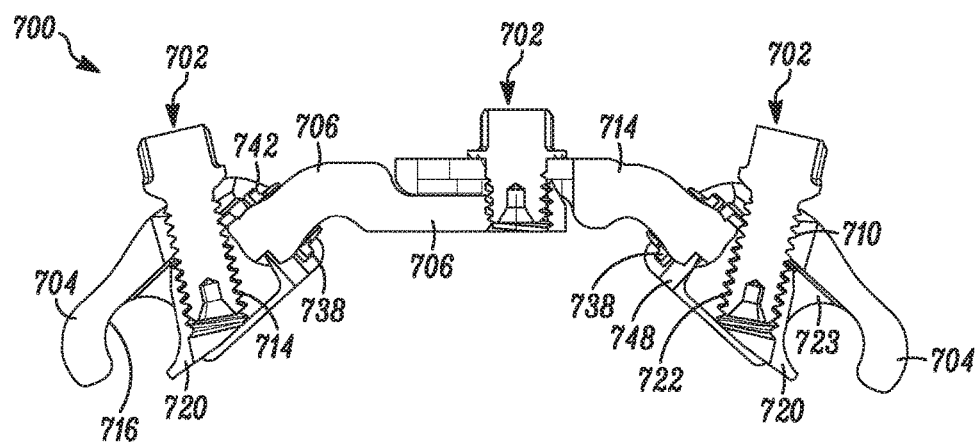
FIG. 52 is a cross section view of arched transverse connector of FIG. 51.

FIGS. 49-50 illustrate another example embodiment of an arched transverse connector 600. The arched transverse connector 600 is assembled during a surgical procedure to two rods and provides support between at least two rods that form a part of a spinal fixation assembly (for an example, refer to FIG. 72). The arched transverse connector 600 includes an eccentric pin 602, a pair of connector heads 604, and connector bridge 606.

The transverse connector 600 is generally arched (as best viewed in FIG. 50) with the center axis of the connector bridge following a radial arc. The generally arched shape of the transverse connector 600 assists in avoiding any unnecessary dural impingement once the arched transverse connector 600 is implanted, particularly when the arched transverse connector 600 is assembled to a posterior spinal fixation assembly. Preferably, the arched transverse connector 600 is composed of a metal (e.g. titanium, stainless steel, etc.), but may also be of a polymer (e.g. poly-ether-ether-ketone (PEEK)) or any other material suitable for the applications of the present invention. Additionally, the arched transverse connector 600 may be composed of a combination of both metal and polymer materials.

This embodiment has minimal moving parts so that a clinician may optionally perform a minimal amount of adjustments to secure the arched transverse connector 600 to a pair of rods. Each connector head 604 includes an eccentric pin 602 that is retained within a cavity 608 of the housing by a retaining c-ring 610. The cavity 610 extends generally perpendicular from the front surface 612 of the connector head 604 to at least partially through the connector head 604. The retaining c-ring 610 and eccentric pin 623 have essentially the same features and functions as the retaining c-ring 518 and eccentric pin 514 of the first embodiment of the arched transverse connector 500, such that their descriptions will not be repeated here. Similarly, the connector heads 604 (which include, for example, positioning indicators 614 and annular recess 616) have essentially the same features and functions as the connector heads 506 of the first embodiment of the arched transverse connector 500, such that their descriptions will also not be repeated here.

FIGS. 51-55 illustrate another example embodiment of an arched transverse connector 700. The arched transverse connector 700 is assembled during a surgical procedure to two rods (e.g. rods 60) and provides support between at least two rods that faun a part of a spinal fixation assembly (for an example, refer to FIG. 72). This embodiment of the arched transverse connector 700 enables the user to configure it in a multitude of configurations so that the arched transverse connector 700 may best accommodate the rods that it may attach to. The arched transverse connector 700 includes set screws 702, a pair of housings 704, connector arms 706, and a set of securing blocks 708. The arched transverse connector 700 has a number of adjustable connections, including; between the two connector arms 708, and between the housings 706 and connector arms 708. These adjustable connections enable various degrees of movement and linear translation of the arched transverse connector 700, which will be discussed in more detail below.

The transverse connector 700 is generally arched (as best viewed in FIGS. 51 and 52) with the center axis of the connector arms 706 following a radial arc. The generally arched shape of the transverse connector 700 assists in avoiding any unnecessary dural impingement once the arched transverse connector 700 is implanted. This is particularly the case when the arched transverse connector 700 is assembled to a posterior spinal fixation assembly. Preferably, the arched transverse connector 700 is composed of a metal (e.g. titanium, stainless steel, etc.), but may also be of a polymer (e.g. poly-ether-ether-ketone (PEEK)) or any other material suitable for the applications of the present invention. Additionally, the arched transverse connector 700 may be composed of a combination of both metal and polymer materials.

The housing 704 includes a partially threaded cavity 710 which extends generally at an angle from the front surface 712 of the housing 704 to at least partially through the housing 704. The partially threaded cavity 710 provides at least one internal helical thread 714 for the engaging and advancing a set screw 702 into the housing 704. The advancement of the set screw 702 into the housing 704 assists in binding the securing block 708 and a rod captured within the arched recess 716 of the housing 704, as will be described in greater detail below.

Permanently securing the placement of rods within the arched recesses 716 involves further engagement of the set screws 702 into the housings 704 and associated securing blocks 708. When a set screw 702 is further engaged into a housing 704 and associated securing block 708, the securing block 708 binds a number of components within the arched transverse connector 700. This ultimately results in the secure engagement of a rod within the arched recesses 716 and locking the configuration of the arched transverse connector 700, which will be discussed in more detail below. Although the arched recesses 716 are shown as having an arched profile, any size and shaped recess suitable for securing any size and shaped rod can be implemented into the housing 704 without departing from the scope of the present invention.

At least one exterior helical thread 714 radially extends from the outer surface of the set screw 702 which allows the set screw 702 to engage and advance into the housing 704. Upon advancement of the set screw 702 along its central axis into the housing 704 and associated securing block 708, the securing block becomes bound into the housing 704. The set screw 702 threadably engages the securing block 708 by way of the threaded through hole 718 of the securing block 708. If a rod is captured within the arched recess 716, the securing block also secures the rod within the arched recess 716. The securing block includes a tongue 720 which at least partially functions to capture and securely engage a rod within the arched recess when the securing block 708 is bound to the housing 704. Surface features on the engagement surfaces 722 of the securing blocks 708 and on the arched recesses 716 may be used to increase the frictional engagement between the securing blocks 708, housing 704, and rods.

Engagement of a set screw 702 into the housing 704 and associated securing block 708 also locks the configuration between the housing 704 and the adjacent connector arm 706. The distal end of a connector arm 706 includes a spherical joint 724 and a keying feature 726. The spherical joint 724 enables the connector arm 706 to articulate relative to the housing 704. The keying feature 726 restricts the radial articulation of the housing 704 relative to the connector arm 706 so that there is not an unnecessary amount of articulation between the connector arm 706 and housing 704. By way of example, the housing 704 is able to rotate approximately 20 degrees in both directions relative to the connector arm 706. The keying feature 726 restricts the rotational movement by mating with the key slot 728 in the housing 706, which provides limited space for the keying feature 726 to rotate. This provides a user with the ability to make relatively slight configuration adjustments between the housing 706 and connector arm 704, while not making the adjustable connection too cumbersome for the user.

The connector arms 706 mate with each other at their medial ends, where a set screw 702 controls the locked and unlocked configuration between them. Both connector arms have features at their medial ends which function to enable the connector arms 706 to linearly translate relative to each other as well as slightly angle themselves relative to each other. The features which function to guide and limit the translation and angulation between the connector arms 706 may be any feature necessary to enable the configuration between the two connector arms 706 without departing from the scope of this invention. By way of example, a first connector arm may have a threaded hole 732 (shown best in FIG. 53) that enables a connector arm set screw 702 to engage. The loosening and tightening of the set screw 702 would allow the second connector arm 706 to linearly translate to either expand or shorten the distance between the housings 704. By way of example only, the distance between the center of the arched recesses 716 may range approximately between 40-75 mm (and shown as dimension X in FIG. 51).

A slot 732 extending across at least part of the second connector arm 706 enables the relative linear translation between the two connector arms 706, while also limiting their linear translation to the confines of the slot 732. Additionally, the extruded guide 734 assists in maintaining alignment between the connector arms by mating with the slot 732. The extruded guide 734 is not completely circular in cross section and, instead, includes flat extensions 736 (best shown in FIG. 54) which limit the relative angulations between the two connector arms 706. By way of example, the connector arms 706 are able to angle approximately 15 degrees in either direction about the center axis of the threaded hole 730. This provides a user with the ability to make configuration adjustments between the housing 704 and connector atm 706, while not making the adjustable connection too cumbersome for the user. Generally, the medial ends of both of the connector arms 706 have relatively flat surfaces in order to accommodate smooth linear translation between their mating features (i.e. extruded guide 734 and slot 732).

Figure 53:
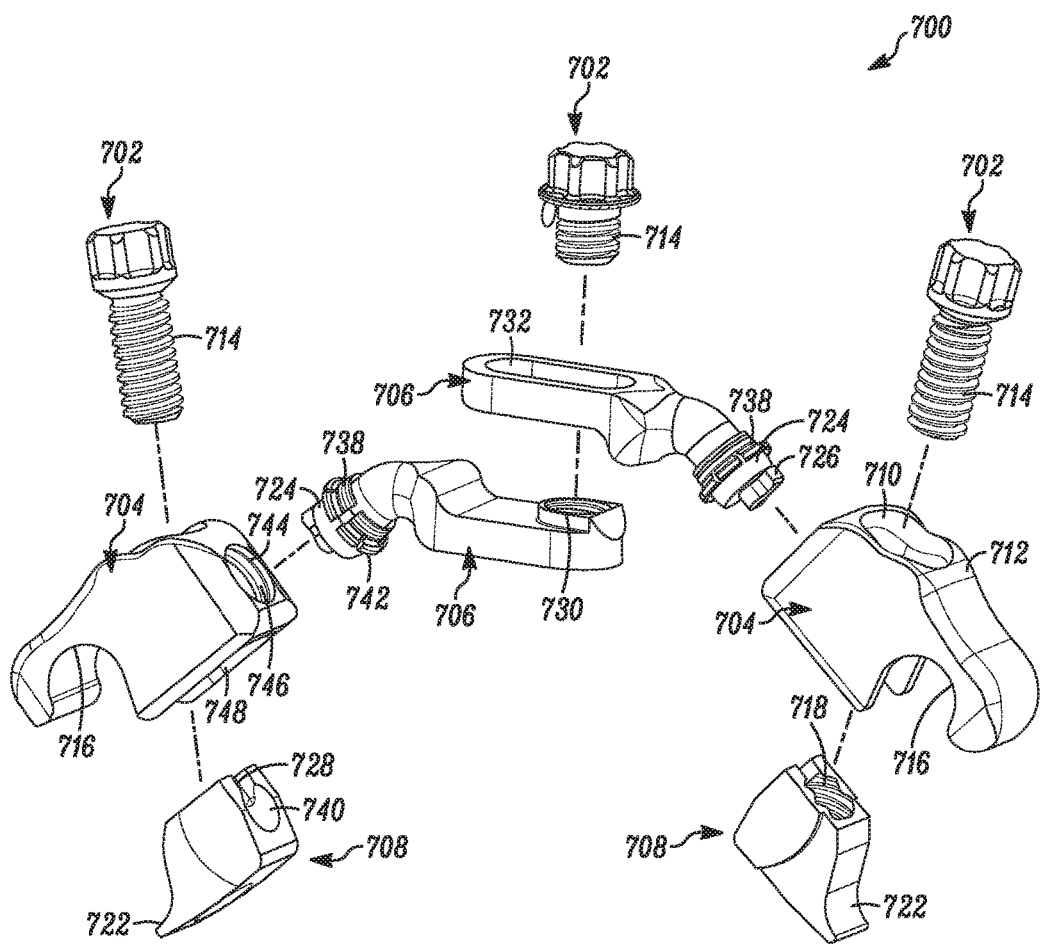
FIG. 53 is an exploded view of the arched transverse connector of FIG. 51.
Figure 54:
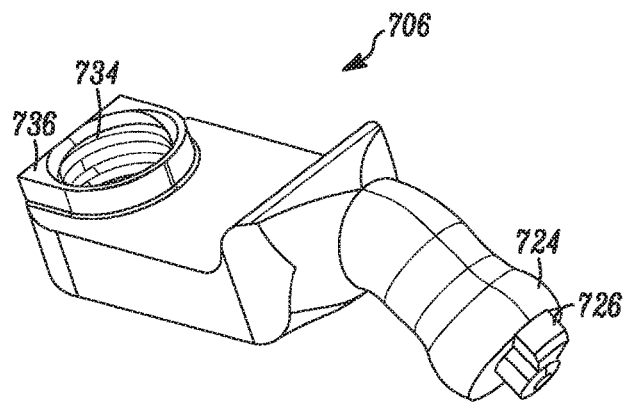
FIG. 54 is a perspective view of a slide arm of the arched transverse connector of FIG. 51.
Figure 55:
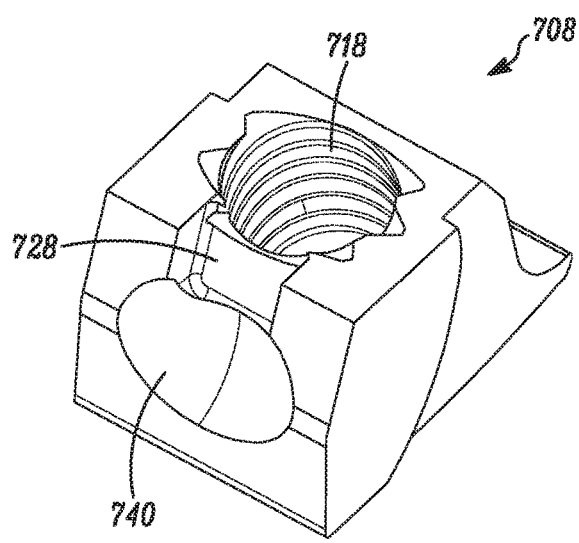
FIG. 55 is a perspective view of a securing block of the arched transverse connector of FIG. 51.
Figure 56:
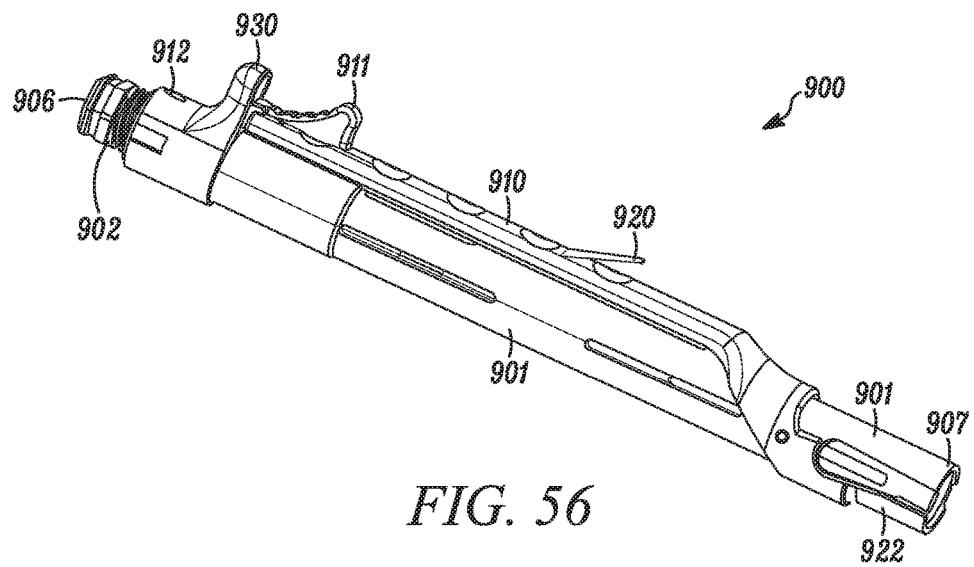
FIG. 56 is a perspective view of a reduction tower, according to an example embodiment.
Figure 57:
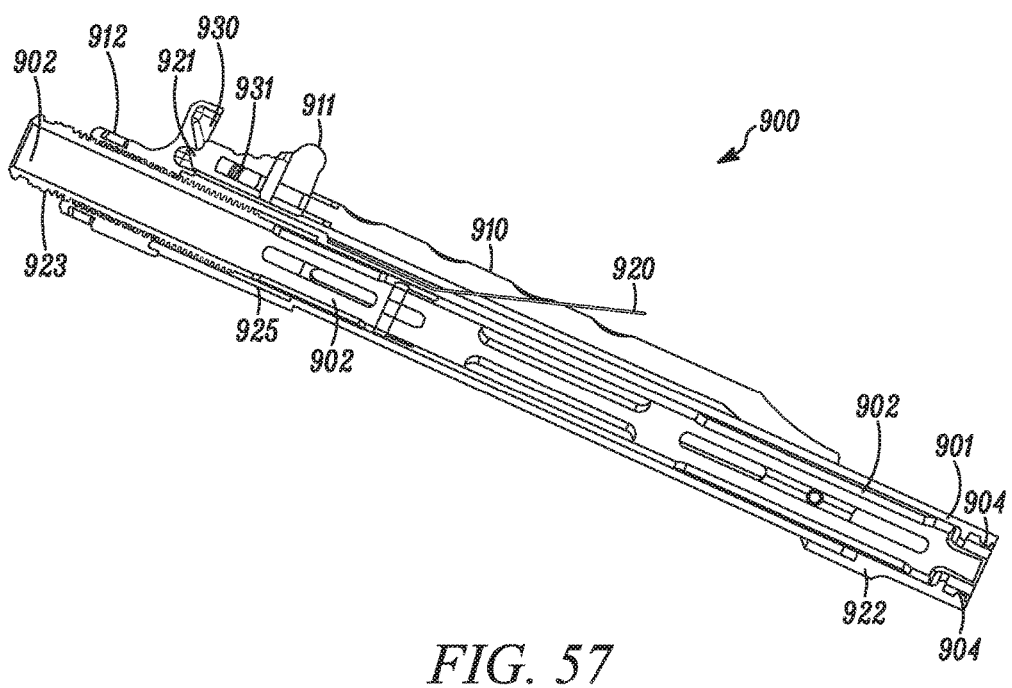
FIG. 57 is a cross section view of the reduction tower of FIG. 56.

As best shown in FIG. 53, a split collar 738 is secured around the distal end of the connector arm 706. The split collar 738 functions to enable the spherical joint 724 to articulate within the spherical socket 740 of the securing block 708 while maintaining a secure connection between the connector arm 706 and the housing 704. Flanges 742 radially extending from the split collar 738 mate with an annular step 744 located in the inside walls of the side through hole 746 of the housing 704.

As mentioned above, when the housing set screws 702 are engaged into their associated housings 704 and securing blocks 708, the securing blocks 708 ultimately become fixed within the housings 704. When a securing block 708 becomes fixed within a housing 704, the securing block 708 also fixes the jointed configuration between the adjacent housing 704 and connector arm 706. The further engagement of the set screw 702 into the securing block 708 causes the securing block 708 to bind into the housing cavity 748 which ultimately securely engages the distal end of the adjacent connector arm 706. Ultimately, the securing block 708 forces against the distal end of the connector arm 706 (which pushes the connector arm 706 in a direction away from the housing 704) until the split collar 738 restricts any further movement of the connector arm 706. The split collar 738 is confined to expanding only to the size of the annular step 744, which is sized to restrict the split collar 738 from expanding enough to allow the distal end of the connector arm 706 from losing its connection with the housing 704. By way of example, when the housing set screw 702 is generally fully engaged within the housing 704 and associated securing block 708, the securing block 708 is forcing the permanent fixation of the connector arm 706 relative to the housing 704. Furthermore, secure fixation of a securing block 708 within a housing 704 also secures a rod captured within the adjacent arched recess 716, as described above.

Figure 58:
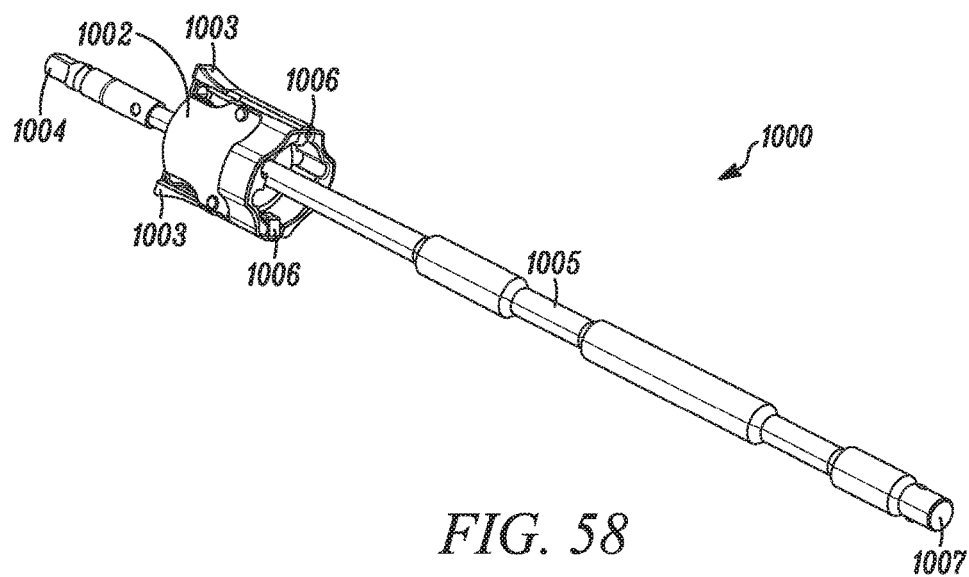
FIG. 58 is a perspective view of a locking tool according to one example embodiment for use with the spinal anchor assembly of FIG. 1.
Figure 59:
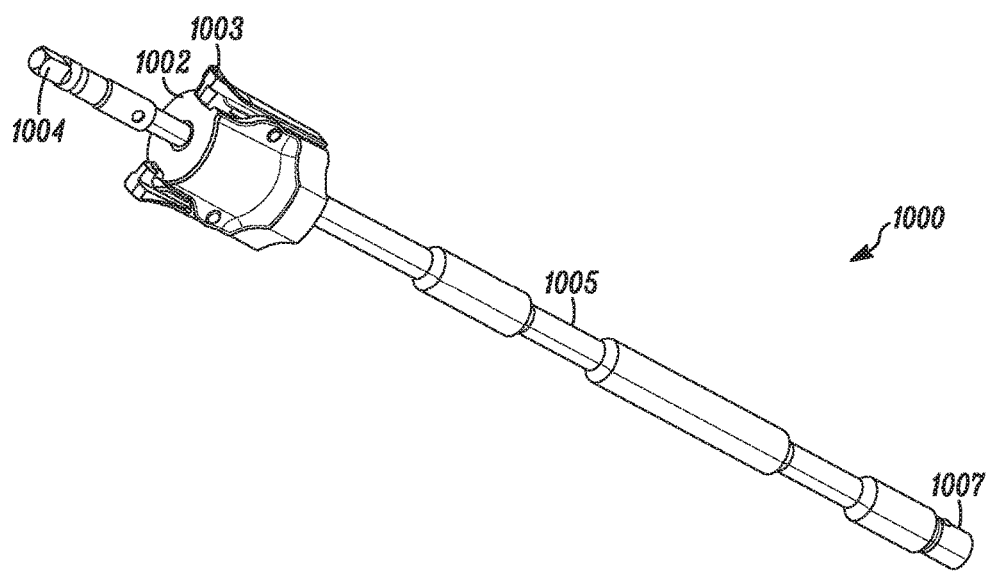
FIG. 59 is another perspective view of the locking tool of FIG. 58.
Figure 60:
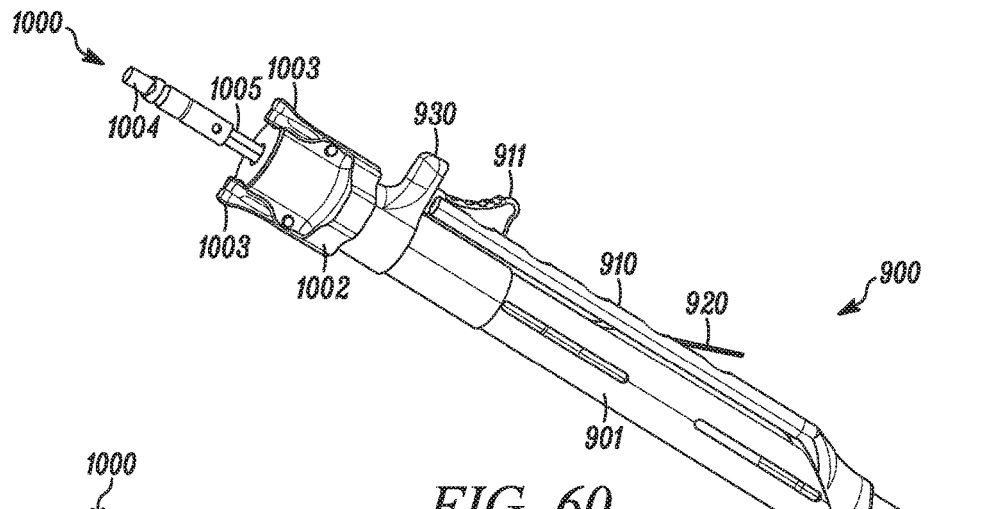
FIG. 60 is a perspective view of one example of a tooling assembly, according to a first embodiment of the present invention.
Figure 61:
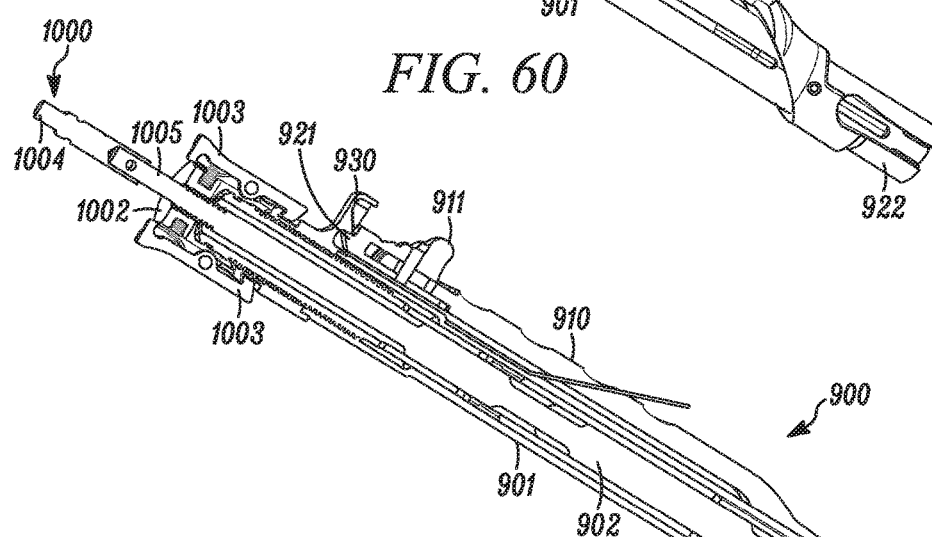
FIG. 61 is a cross section view of a tooling assembly of FIG. 60.
Figure 62:
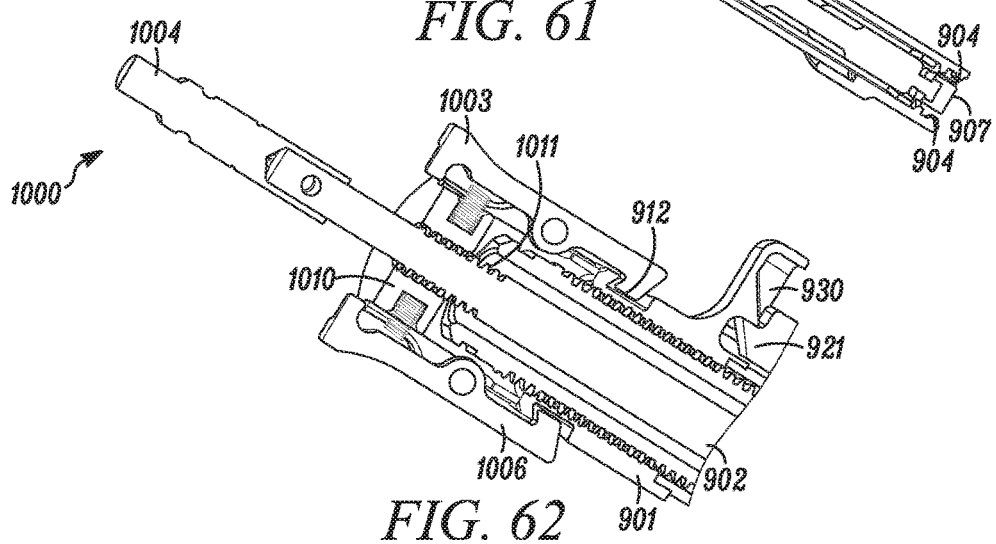
FIG. 62 is a partial cross section view of a tooling assembly of FIG. 60.

FIGS. 56-64 illustrate an example of an embodiment of a reduction tower 900. The reduction tower 900 comprises a proximal end 906 and a distal end 907 and includes a housing 901, an interior shaft 902, and a grasping element 910. The housing 901 and interior shaft element 902 are both hollow to allow the passage of various tooling and/or parts through their centers, generally along their shared longitudinal axis. By way of example, a locking tool 1000 (as shown in FIGS. 58 and 59) may be inserted through the center of the housing 901 and interior shaft 902 and attached at the proximal end of the housing 901 to form a tooling assembly 1100 (as shown by way of example in FIGS. 60-62). This tooling assembly 1100 can be used to lock a bone screw assembly configuration (as described herein), and will be discussed in more detail below. A variety of tooling and parts may be combined with the reduction tower 900 to perform a variety of functions, as described below. Furthermore, the reduction tower 900 may also function to lock bone screw configurations without the addition of accessory tooling (i.e. locking tool 1000), which will also be discussed in more detail below.

The grasping element 910 of the reduction tower 900 includes a spring element 920, a finger grip 911, a latch 921, and a grasping arm 922. Grasping features 904 are located at the distal end of the grasping arm 922 and housing 901 and function to engage, for example, the receiver 20 (of receiver assembly 12) of a anchor assembly 10. One advantageous use of the reduction tower 900 is the ability to lock any of the provisional locking screws without using a closure structure.

As described above, when the bone screw assembly 10 is secured to a bony structure in its unlocked position, the receiver assembly 12 can articulate freely relative to the bone screw 11. After determining the necessary orientation of the receiver assembly 12 relative to the bone screw 11 to receive the rod and positioning the rod in the receiver, the clinician may use the reduction tower 900 to provisionally lock the bone screw assembly 10 orientation without using a closure member.

To provisionally lock the bone screw assembly 10, for example, the clinician positions the open (unlocked) distal end 907 of the reduction tower 900 adjacent and generally concentric to the receiver assembly 12 of the spinal anchor assembly 10. The user then advances the distal end 907 of the reduction tower 900 over at least a portion of the receiver assembly 12 and generally aligns the grasping features 904 of the reduction tower 900 with the tool engaging features (i.e. grip bores 21) of the receiver 20. The clinician then locks the reduction tower 900 by compressing the grasping element 910 towards the housing 901, for example, by pressing on the grasping arm 922 until the latch 921 engages the latch keeper 930. When the latch 921 is fully engaged with the latch keeper 930, the grasping features 904 can fully engage the tool engaging features of the receiver 20 (as illustrated in FIGS. 58 and 59), thus securing the receiver 20 within the distal end 907 of the reduction tower 900.

Once the reduction tower 900 is securely mated to the receiver assembly 12 of a spinal anchor 10, the interior shaft 902 can be advanced in the direction of the distal end 907 of the reduction tower 900. This can be accomplished in a number of different ways, such as, for example, by attaching a T-handle or a torquing tool (not shown) to the proximal end of the interior shaft 902 and forcing the interior shaft 902 to rotate along its longitudinal axis. At least a portion of the interior shaft has exterior threads 923 that engage interior threads 925 along at least a portion of the interior wall of the housing 901 (and best shown in FIG. 62). This threaded engagement allows the interior shaft 902 to translate along its longitudinal axis relative to the housing 901 when the interior shaft 902 is rotated in either direction.

Figure 63:
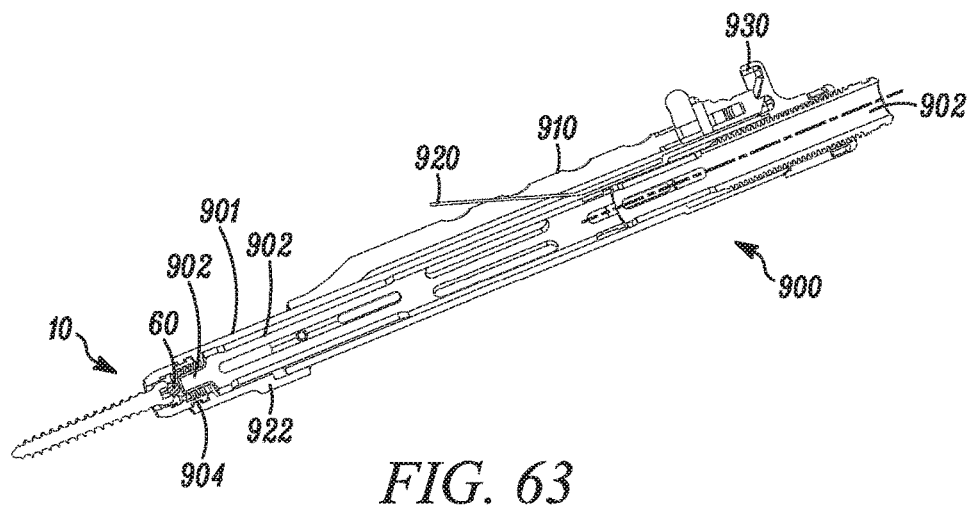
FIG. 63 is a perspective section view of one example of a reduction tower grasping a spinal anchor assembly and reducing a rod.
Figure 64:
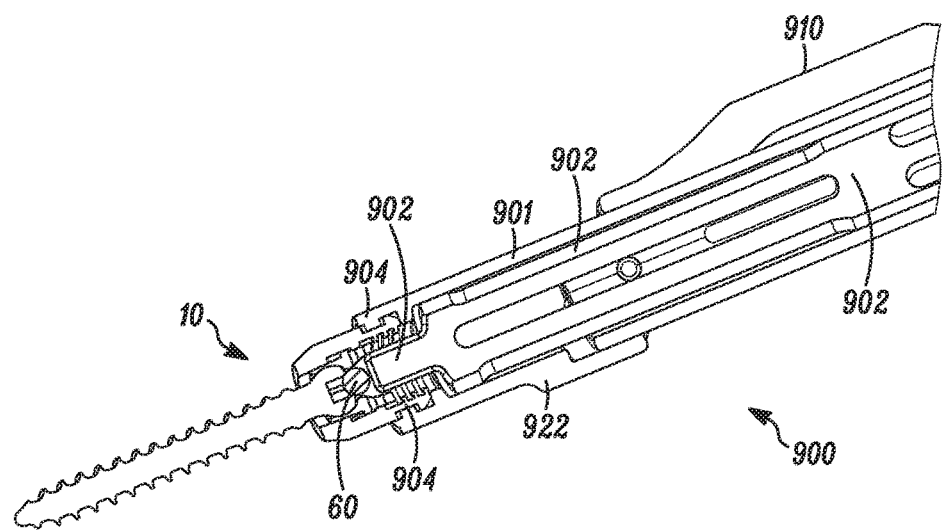
FIG. 64 is a perspective partial section view of one example of a reduction tower grasping a spinal anchor assembly and reducing a rod.

As depicted in FIGS. 63-64, in order to lock the configuration of the spinal anchor assembly 10, the interior shaft 902 is advanced in the direction of the distal end 907 of the reduction tower 900. The interior shaft 902 is advanced until the distal end of the interior shaft 902 is forcing down upon the rod (such as a rod 60) captured within the receiver assembly 12 (and best shown in FIGS. 63 and 64). The distal end of the interior shaft 902 continues to force down upon the rod until the collet 40 has securely wedged itself into the receiver 20 such that the bone screw 11, collet 40 and receiver 20 are no longer able to move independently of each other. As described above, when the collet 40 becomes securely wedged into the receiver 20, the collet 40 compresses and secures the capture structure 16 of the bone screw 11 within its interior spherical surface 49. By way of example, a feature within the reduction tower 900 may produce an audible indicator (i.e. a clicking sound) once the interior shaft 902 has advanced the necessary distance to lock the configuration of the spinal anchor assembly 10. Any number of different mechanisms or features (i.e. visual markers, break-away torquing tool adapters) may be used to indicate to the user that the interior shaft 902 has advanced far enough so that the spinal anchor assembly 10 is now locked into its configuration, without departing from the scope of the present invention.

Once the interior shaft 902 has advanced the necessary distance to lock the configuration of the bone screw assembly 10, the user may then advance the finger grip 911 to release the latch 921 from the latch keeper 930, thus unlocking the grasping element 910 and releasing the engagement between the reduction tower 900 and receiver assembly 12. The rod used to lock the configuration of the bone screw assembly 10 can then be removed from the receiver assembly 12, as necessary, while the spinal anchor assembly 10 remains in the locked configuration. This allows the clinician to use the spinal anchor assembly 10, for example, as a tool to assist in positioning the spine (i.e. de-rotation of the spine) and correcting spinal deformities. A rod may be secured within the receiver assembly 12 at a later time when the user is prepared to secure the positioning of the bone screw assembly 10 relative to an rod.

Optionally, and by way of example, a locking tool 1000 may be adapted to the reduction tower 900 to lock the spinal anchor assembly 10 into a desired configuration. The locking tool 1000 may be used instead of the distal end of the interior shaft 902 to lock the configuration of the bone screw assembly 10. By way of example, the locking tool 1000 may be adapted to the reduction tower 900 by inserting its distal end into the proximal end 906 of the reduction tower 900 (through the hollow centers of the housing 901 and interior shaft 902). The distal end of the locking tool 1000 is advanced through the reduction tower 900 until the adapter 1002 of the locking tool 1000 is securely engaged to the proximal end 906 of the reduction tower 900. The adapter 1002 includes two spring clips 1003 that allow the adapter 1002 to slide over the proximal end of the reduction tower 900 and engage the engaging ends 1006 of the spring clips 1003 into the tool locking features 912 at the proximal end of the housing 901. The engaging ends 1006 of the spring clips 1003 mate with the tool locking features 912 of the housing 901 such that the locking tool 1000 is constrained from movement relative to the reduction tower 900, both rotationally and along their shared longitudinal axis.

Once the locking tool 1000 is securely engaged at the proximal end 906 of the reduction tower 900, a torquing tool (not shown), for example, can be adapted to the torque adapter 1004 at the proximal end of the tooling shaft 1005. In order to lock the configuration of the spinal anchor assembly 10, the tooling shaft 1005 is advanced in the direction of the distal end 907 of the reduction tower 900. The tooling shaft 1005 is advanced by rotating the tooling shaft (i.e. by rotating the torque adapter 1004). The locking tool 1000 includes a threaded guide 1010 that functions to assist in the positioning of the tooling shaft 1005. The tooling shaft 1005 also is partially threaded 1011 along a portion of its proximal end. Threaded engagement of the threaded guide 1010 with the tooling shaft 1005 enables the tooling shaft 1005 to linearly translate along its longitudinal axis when rotated along its longitudinal axis.

The tooling shaft 1005 is rotated and advanced toward the spinal anchor assembly 10 until at least a portion of the distal face 1007 is forcing down upon a rod captured within the receiver assembly 12. The distal face 1007 of the tooling shaft 1005 continues to force down upon the rod (which subsequently forced down upon the collet 40) until the collet 40 has securely wedged itself into the receiver 20 such that the bone screw 11, collet 40 and receiver 20 are no longer able to move independently of each other. Any number of different mechanisms or features (i.e. visual markers, break-away torquing tool adapters) may be used to indicate to the user that the tooling shaft 1005 has advanced far enough so that the bone screw assembly 10 is now locked into its configuration, without departing from the scope of the present invention.

Furthermore, the distal end of the locking tool 1000 is shaped and dimensioned such that it may advance into a receiver assembly 12 and lock the configuration of the associated bone screw assembly 10 without a rod captured within the receiver assembly 12. This is accomplished generally similar to the steps for locking the configuration of the bone screw assembly 10, as described above, but instead of the distal face 1007 of the tooling shaft 1005 forcing down on a rod, the distal face 1007 forces down upon generally the top surface 41 of the collet 40. As described above, the tooling shaft 1005 is advanced until the collet 40 is securely wedged within the receiver 20, thus locking the configuration of the bone screw assembly 10.

The tooling assembly 1100 may be disassembled by compressing the spring clips 1003, thus disengaging the engaging ends 1006 of the spring clips 1003 from the locking tool 1000. The locking tool 1000 may be removed from the tool locking features 912 at the proximal end of the housing 901. This releases the rotational and translational fixation between the locking tool 1000 and the reduction tower 900 so that the locking tool 1000 can slide out and away from the reduction tower 900. The locking tool 1000 may be assembled to the reduction tower 900 before, during, or after the reduction tower 900 becomes securely engaged to a receiver assembly 12. Furthermore, the reduction tower 900 may adapt and remove any number of various tooling throughout its use without departing from the scope of this invention.

When necessary, the receiver 12 may be released from the distal end 907 of the reduction tower 900 by advancing the finger grip 911 towards the distal end. A spring 931 is housed within the finger grip 911 which forces the finger grip 911 back to its original position once the user is no longer forcing it towards the distal end of the reduction tower 900. Although shown as a spring 931, any number of features may be associated with the finger grip 911 and/or latch 930 to allow the user to release the grasping element 910 from its locked position, without departing from the scope of this invention.

The grasping arm 922 is spring loaded by means of a cantilever spring 920, but may be spring loaded using any number of elements that force the grasping arm 922 back to its original unlocked position. Although a cantilever spring 920 is shown in this example, any number of features or mechanisms may be used to assist in controlling the movement and placement of the grasping arm 922 without departing from the scope of this invention.

Figure 65:
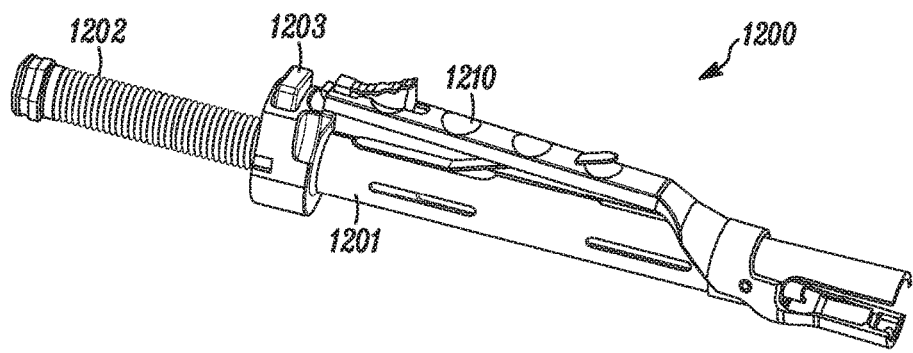
FIG. 65 is a perspective view of one example of a reduction tower, according to a second embodiment of the present invention.
Figure 66:
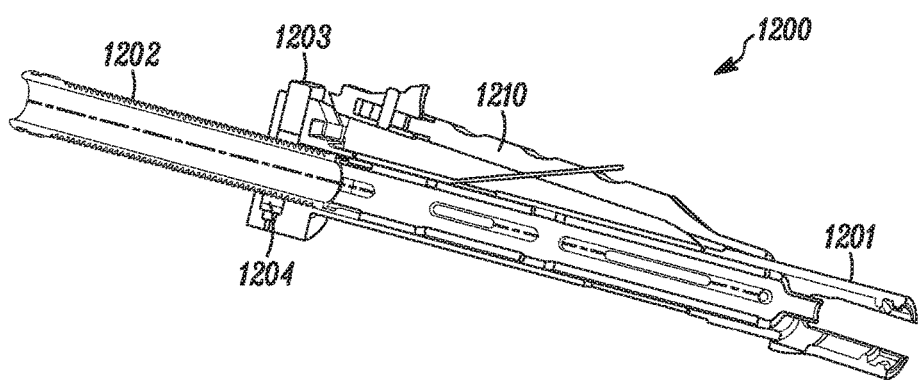
FIG. 66 is a cross section view of the reduction tower of FIG. 65.
Figure 67:
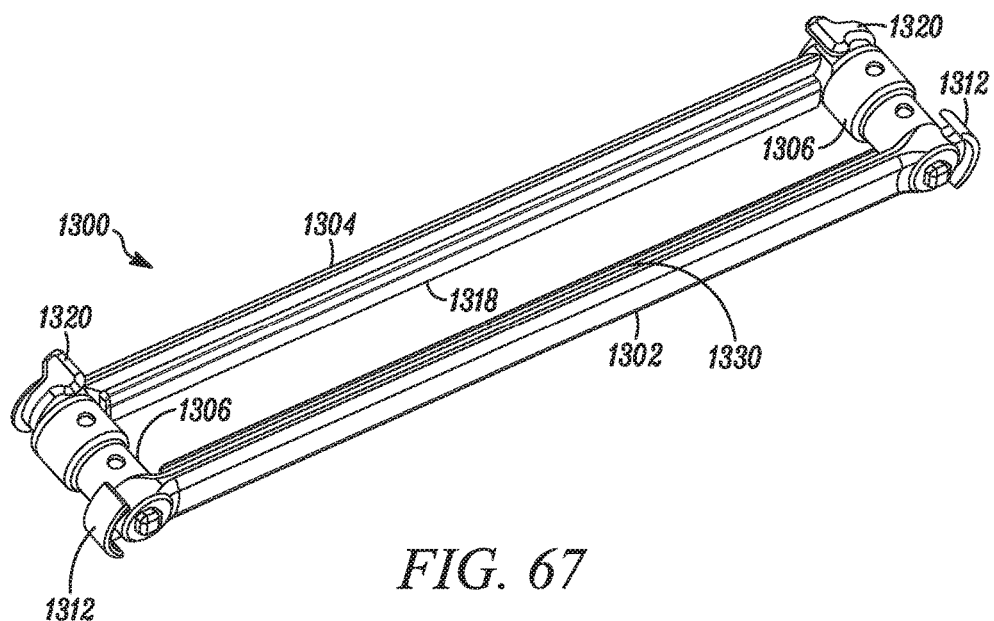
FIG. 67 is a perspective view of the reduction tower link in the open position.
Figure 68:
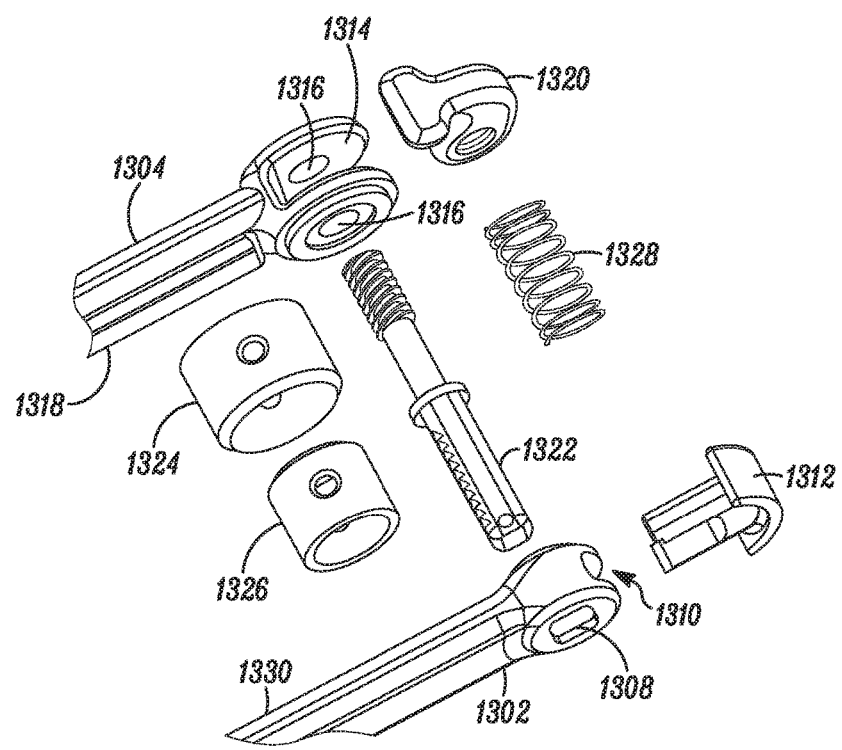
FIG. 68 is an exploded perspective view of the reduction tower link of FIG. 67.

FIGS. 65-66 illustrate an example of a second embodiment of a reduction tower 1200. The reduction tower 1200 includes a housing 1201, an interior shaft 1202 and a grasping element 1210. This second embodiment of a reduction tower 1200 is essentially the same in features and functions as the first embodiment of a reduction tower 900, as described in detail above. Therefore, a repeated discussion of the similar features and functions of the reduction tower 1200 will not be repeated here. However, the reduction tower 1200 presented herein includes a release button 1203. The release button 1203 functions to position a partially threaded 1204 feature relative to the interior shaft 1202. The positioning of the partially threaded 1204 feature enables either a guided or free linear translation of the interior shaft 1202. By way of example, engaging the release button 1203 disengages the partially threaded 1204 feature from its threaded engagement with the interior shaft 1202. This enables the interior shaft 1202 to freely and quickly linearly translate along its longitudinal axis relative to the housing 1201. This is desirable for quick positioning of the interior shaft 1202 relative to the housing 1201. By way of further example, disengagement of the release button 1203 engages the partially threaded 1204 feature to the exterior threads on the outer wall of the interior shaft 1202. This threaded engagement limits the linear translation of the interior shaft 1202 relative to the housing 1201 to only when the interior shaft 1202 is being rotated along its longitudinal axis.

For instances in which de-rotation of one or more vertebral bodies is desired, a reduction tower link 1300 is also provided. In accordance with a preferred embodiment of the present invention, engaging the reduction tower link 1300 to two or more reduction towers 900 allows derotation of all of the vertebrae together via a ratcheting mechanism. As shown in FIGS. 67-71, the reduction tower link 1300 includes a stationary arm 1302, a moving arm 1304, and a ratchet mechanism 1306. Stationary arm 1302 further comprises a terminal groove 1308 and a receiving aperture 1310 at either end. The terminal grooves 1308 are sized and dimensioned to receive a ratchet pawl 1312. Ratchet pawl 1310 is spring-loaded 1328 to engage the moving arm 1304 (or ratchet arm). The aperture 1310 is sized and dimensioned to receive the ratchet post 1322 as described below. Additionally, the inner face 1330 of the stationary arm 1302 is comprised of a softer, malleable material (including, but not limited to, silicone) to provide leeway as reduction tower link 1300 interacts with the reduction towers 900.

The moving arm (or ratchet arm) 1304 also contains terminal grooves 1314 and a receiving aperture 1316 at either end as well as a malleable inner face 1318. The terminal grooves 1314 which are sized and dimensioned to receive a final lock nut 1320. As the final lock 1320 is turned, it draws the ratchet post 1322 through its receiving aperture 1316. The inner face 1318 is also comprised of a softer, malleable material (including, but not limited to, silicone) to provide leeway as the reduction tower link 1300 interacts with the reduction towers 900.

Ratcheting mechanism 1306 contains an inner ratchet post 1322 and an outer portion comprised of an outer cylinder 1324 and an inner cylinder 1326.

Figure 69:
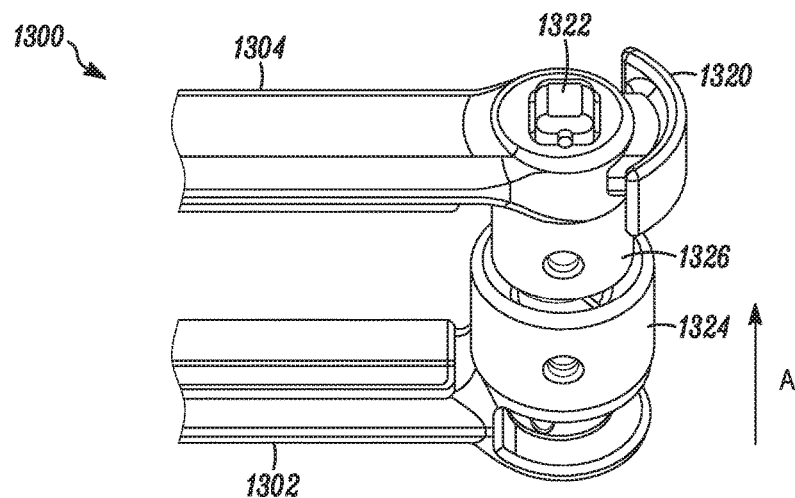
FIG. 69 is a detailed view of the ratcheting mechanism of the reduction tower link of FIG. 67.
Figure 70:
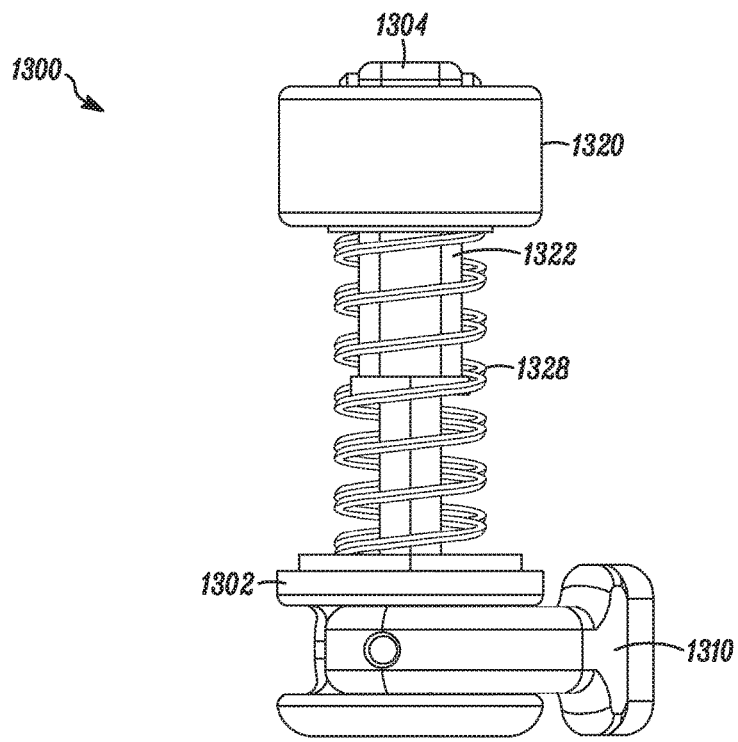
FIG. 70 is a detailed view of the ratcheting mechanism with the outer and inner cylinders of FIG. 67 removed.
Figure 71:
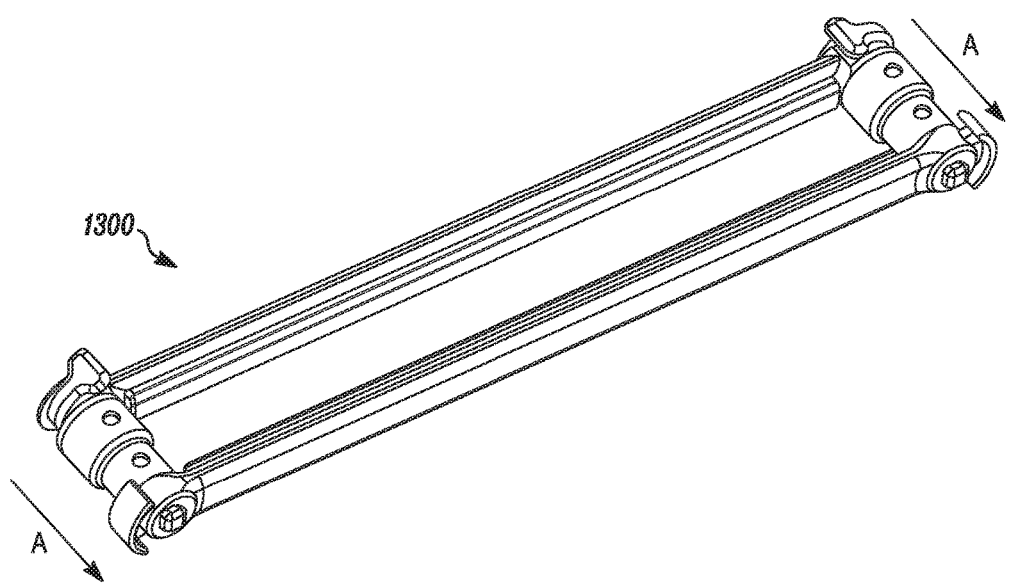
FIG. 71 is a perspective view of the reduction tower link of FIG. 67 with arrows indicating the direction of movement when the arms are squeezed together.

As depicted in FIGS. 69 and 71, squeezing the arms 1302, 1304 together causes the ratchet 1306, moving arm 1304, and inner cylinder 1326 to move towards the stationary arm 1302 as indicated as arrow A. The spring-loaded ratchet pawl 1312 prevents release of the ratcheting mechanism 1306. The final lock nuts 1320 may be tightened to achieve final positioning of the reduction tower link 1300. Pushing the ratchet pawl 1312 disengages the spring-loaded mechanism and releases the arms 1302, 1304.

According to a second embodiment, instead of a ratcheting mechanism, a cam may be used to bring the stationary arm 1302 and moving arm 1304 together around the reduction towers 900. A knob on each arm 1302, 1304 may be used to adjust the distance between the bars 1302, 1304 in addition to the travel created by the cams.

An example surgical procedure is described below for use with, for example, the anchor systems and related tools described herein. The surgical procedure described herein is not intended to be exhaustive, such that additional steps that are not discussed herein may be incorporated to the procedure without departing from the intended scope.

The procedure begins, in pertinent part, by placing a spinal anchor (e.g. bone screw 11) into each of a plurality of pedicles. For each pedicle, the desired entry point is located and the cortex is perforated using an awl or burr. Next, a pilot hole is created by passing, for example, a narrow or lumbar gearshift prove through the pedicle and into the vertebral body. Care should be taken to ensure the instrument(s) do not breach the cortical wall of the pedicle, as the pilot hole will ultimately determine the final position of the screw. The pilot hole should be inspected for perforations by using a ball-tip probe to palpate the pedicle wall on all sides. Pedicle markers may also be placed into the pilot holes followed by lateral and anterior-posterior imaging to verify proper positioning.

In patients with dense bone or where tapping is preferred, depth gauging may be accomplished using the markings on the instrument shaft in conjunction with fluoroscopy. If depth gauging is performed, the ball-tip probe should again be used to inspect the pilot hole for perforation. After the appropriate screw length is determined, a screwdriver is used to drive the screw into the pilot hole and advance it until the desired depth is reached. A screw adjuster may be used if subsequent x-ray or fluoroscopy indicate that screw depth adjustment is necessary.

After the spinal anchors (e.g. bone screw 11) and receiver assemblies (e.g. receiver assembly 12) are secured to the desired pedicles, the rods 60 are prepared for placement. The systems described herein include an array of straight and pre-bent (lordosed) rods. Measurements are taken to determine the appropriate rod lengths using a rod template. The corresponding straight or pre-bent rod from the implant tray may then be selected and additional contouring may be performed as needed with any one of an array of rod benders: (e.g., French benders, in-situ sagittal benders, in-situ coronal benders, and plate style benders).

A rod holder may then be used to sequentially insert the rod 60 into each of the receiver assemblies (e.g. receiver assemblies 12) until the rod 60 is lying at the bottom of all of the receiver assemblies 12. With a portion of a rod 60 fully seated in the receiver assemblies 12, capture structures (e.g. capture structure 16) are engaged into the receiver assemblies 12. By way of example, the clinician aligns the recessed slot 75 of the closure structure 13 with the recessed slot 24 of the receiver (e.g. receiver 20). The alignment of the recessed slots 24, 75 prevents incorrect engagement of the interior and exterior guide and advancement structures. Alternately, a lock screw starter guide may be used to capture the receiver assembly 20 (or closure structure 13) followed by introduction of the lock screw starter.

If the rod 60 is difficult to fully seat in the receiver assembly 120, the rod 60 may be reduced using, for example, a rocker, persuader, or reduction tower 900, 1200. When only a small amount of reduction is required, the rocker or the persuader is preferably utilized. Using the rocker, the receiver assembly 12 is grasped via the oval grip bores 21 on either side of the receiver assembly 20. The rocker may then be deflected downward until the spinal anchor assembly 10 is levered up and the rod 60 is fully seated into position within the receiver assembly 12. A closure structure 13 may then be inserted using a lock screw starter. Alternatively, a persuader may be used. To do so, the tip of the persuader is slid over the top of the receiver assembly 12. To reduce the rod 60, downward force is applied to the persuader while compressing the handle ratchet closed. Once the rod 60 is fully seated in the receiver assembly 12, a lock screw starter may be used to place the closure structure 13. The persuader may be disengaged from the receiver assembly 12 by releasing the ratchet and pulling up on the persuader.

A reduction tower 900 is preferably used whenever a large amount of reduction is required. Prior to using the reduction tower 900, the grasping element 910 should be in the open position. To use the reduction tower 900, the distal end 907 is placed over the rod 60 and around the receiver assembly 112 so that the grasping elements 910 rest on the capture structure 16 and the oval grip bores 21 are aligned. The receiver assembly 112 may be grasped via the grasping features 904 on the grasping element 910 by slowly closing the grasping element 910 towards the housing 901 as described above. With the reduction tower 900 securely engaged with the screw 11, the T-handle attached to the proximal end 906 of the reduction tower 900 may be slowly turned until the rod 60 is fully seated in the capture structure 16. A lock screw starter may be used to insert a closure structure 13 through the interior of the reduction tower 900 to hold the implant 10 in position. Following placement of the closure structure 13, the lock screw starter may be removed, the reduction tower grasping arm 922 may be released and removed from the spinal anchor assembly 10.

According to one aspect, rod rotation and vertebral derotation techniques may be utilized to correct coronal and rotary deformities in the spine. The system of the present invention offers a rod rotation wrench, a reduction tower 900, 1200, and derotation guides (lock screw guides) to perform these operative techniques. In connection with the reduction tower 900, 1200 or a derotation guide, derotation of the spine may be achieved by using these instruments as an extended moment arm to rotate the vertebral bodies in the axial plane.

With the rod 60 fully reduced into the receiver assemblies 12 and the closure structures 13 are placed loosely, the rod 60 may be rotated into its desired position. A rod gripper may be placed over the rod 60 and its handle compressed to achieve rigid fixation. Two rod grippers may be used to transform the coronal deformity into kyophosis or lordosis within the sagittal plane. After the rod 60 has been rotated into the desired position, the closure structures 13 may be tightened.

Rods 60 may be rotated using a rod rotation wrench. The rod rotation wrench may be placed over the hex at the end of the rod 60 and rotated to the desired amount. Vertebral body rotation may be accomplished via the uniplanar, fixed, or provisional locking screws of the present invention. To apply rotational forces to the uniplanar or fixed screws, the lock screw guide is slid over the capture structure 16 of the screw 10. The guide may then be moved in the medial-lateral direction to rotate the vertebral body in the axial plane.

To apply rotational forces to a provisional locking screw, the provisional locking screw must first be locked into a fixed position, preferably using the reduction tower 900. To lock the provisional locking screw, the reduction tower 900 must be rigidly engaged to the capture structure 16 with the rod 60 fully reduced. To do so, a counter-torque instrument may be slid into the tool locking features 912 on the cranial/caudal sides of the reduction tower 900. Next, the locking tool 1000 is inserted into the center of the reduction tower 900 The T-handle attached to the proximal end 906 of the reduction tower 900 may be turned in a clockwise direction until the breakaway torque is achieved. The provisional locking tool may be removed as described above.

With the provisional locking screw in a fixed position, the reduction tower 900 is leveraged in a medial/lateral direction to rotate the vertebral body in the axial plane. Once the amount of de-rotation is achieved, a closure structure 13 may be inserted (preferably using a lock screw starter) and provisionally tightened to hold the rod 60 in a fixed orientation. To minimize the chances of pedicle fracture during vertebral body de-rotation, it is preferable to spread the rotational forces over a series of adjacent pedicle screws. This is accomplished via the reduction tower link 1300 as described above with reference to FIGS. 67-71.

The reduction tower link 1300 is placed over two or more reduction towers 900 such that the reduction towers 900 are positioned between the inner face 1312 of the stationary arm 1302 and the inner face 1318 of the moving arm 1304. Next, the arms 1302, 1304 are squeezed together via the ratcheting mechanism 1306 until the desired amount of vertebral body de-rotation has been achieved. The final lock nuts 1320 may then be tightened to achieve the final positioning of the reduction tower link 1300. Pushing the ratchet pawls 1312 disengages the arms 1302, 1304 so that the reduction tower link 1300 may be removed from the reduction towers 900.

If compression or distraction is desired, the closure structures 13 on one side of the motion segment should be tightened, leaving the other closure structure 13 loose to allow movement along the rod 60. The compressor or distractor may be placed over the rod 60 and against the capture structures 16 of both spinal anchor assemblies 10. With the compressor or distractor properly engaged, the desired amount of compression or distraction may be imparted upon the rods and the second closure structure 13 may be provisionally tightened to hold the construct in position prior to final tightening of the entire construct.

Once the necessary reduction, de-rotation, compression, and/or distraction is achieved, the entire construct is tightened. Beginning with the cephalad screw, the counter-torque is placed over the closure structure 13 until the slots at the distal end of the instrument are completely seated over the rod 60. With a torque T-handle engaged, the lock screw driver is inserted through the counter-torque until it is securely seated in the closure structure 13. Final tightening may then be delivered and these steps may be repeated on the remaining screws.

Next, fixed 600 and adjustable length 500, 700 transverse connectors may be placed to provide torsional stability to the construct. The appropriate length transverse connector is determined preferably by measuring the distance between the rods 60 using measurement calipers. If necessary, transverse connector benders can be used to make fine adjustments to the length of the fixed transverse connectors 600.

According to the embodiment illustrated in FIG. 23, eccentric pins 514 (locking cams) are used to secure the transverse cross connector 500. Prior to inserting the transverse cross connector 500, the eccentric pins 514 should be in the fully open position. To open them, a transverse connector driver is used to rotate both eccentric pins 514 until the positioning indicators 532 are positioned toward the center of the transverse cross connector 500.

With the transverse connector holder still attached, the transverse connector 500 is placed over the rods. Once the connector 500 is seated on both rods 60, a transverse connector driver is used to turn the eccentric pins 514 180 degrees until the positioning indicators 532 on the eccentric pins 514 face laterally and align with the positioning indicator 536. The eccentric pins 514 are then fully locked to the rods 60.

A distractor may be placed over the transverse connector 500 such that it engages the medial aspect of the retaining c-ring 518. Final locking is performed by distracting each ring 518 laterally until it is fully seated as described above.

While not specifically described above, it will be understood that various other steps may be performed in using and implanting the devices disclosed herein, including but not limited to creating an incision in a patient's skin, distracting and retracting tissue to establish an operative corridor to the surgical target site, advancing the implant through the operative corridor to the surgical target site, removing instrumentation from the operative corridor upon insertion of the implant, and closing the surgical wound. Furthermore, procedures described, for example only, may be applied to any region of the spine without departing from the scope of the present invention and dimensioning of the implant may be adjusted to accommodate any region.

While this invention has been described in terms of a best mode for achieving this invention's objectives, it will be appreciated by those skilled in the art that variations may be accomplished in view of these teachings without deviating from the spirit or scope of the invention.

Although described with respect to specific examples of the different embodiments, any feature of the spinal anchor system disclosed herein by way of example only may be applied to any of the embodiments without departing from the scope of the present invention. Furthermore, procedures described, for example only, involving specific regions of the spine (e.g. thoracic and lumbar) may be applied to another region of the spine without departing from the scope of the present invention and dimensioning of the implant may be adjusted to accommodate any region.

What is claimed:

1. A spinal anchor assembly comprising:
   a bone screw;
   a receiver assembly moveably coupled to the bone screw, the receiver assembly comprising a receiver; and
   a collar positioned within the receiver assembly, said collar having a first side and a second side opposing the first side, wherein the first side and the second side are straight and parallel to each other, said collar having a third side and a fourth side opposing said third side, wherein the third side and the fourth side are rounded, and wherein the four sides define an inner cavity; wherein said opposing first and second sides each include a D-shaped facet feature on an interior surface thereof facing said inner cavity; wherein said D-shaped facet feature includes a straight edge portion and a curved portion, wherein the bone screw sits in said collar with a head of the bone screw pivotably coupled to said curved portion of the D-shaped facet feature, wherein the collar is positioned between the head of the bone screw and the receiver such that the head of the bone screw does not directly engage the receiver.

2. The spinal anchor assembly of claim 1, wherein interior surfaces of said opposing third side and fourth side are spherical.

3. The spinal anchor assembly of claim 2, wherein said bone screw further includes a threaded shank, and wherein said head includes opposing fifth and sixth sides and opposing seventh and eighth sides.

4. The spinal anchor assembly of claim 3, wherein said opposing fifth and sixth sides are planar and said opposing seventh and eighth sides are spherical.

5. The spinal anchor assembly of claim 4, wherein said opposing planar fifth and sixth sides engage said facet features of said opposing first and second sides and said spherical opposing third and fourth sides engage said spherical seventh and eighth sides.

6. The spinal anchor assembly of claim 5, wherein said spinal anchor assembly allows articulating movement of said bone screw within a single plane.

7. The spinal anchor assembly of claim 1, wherein the collar further comprises a helical recess on said first side or said second side.

8. The spinal anchor assembly of claim 7, wherein the collar further comprises a plurality of helical recesses on said first side and said second side.

9. The spinal anchor assembly of claim 1, wherein said head of the screw is free to articulate along a single plane relative to said collar.

10. The spinal anchor assembly of claim 1, wherein said collar, said bone screw and said receiver assembly are able to articulate relative to each other along a single plane until they are locked into position.

11. The spinal anchor assembly of claim 10, further comprising:
  a closure structure to lock in a relative position of said collar, said bone screw and said receiver assembly.

12. The spinal anchor assembly of claim 1, wherein said bone screw forms an angle between its longitudinal axis and a longitudinal axis of said receiver assembly of up to 30 degrees in opposite directions.

13. The spinal anchor assembly of claim 12, further comprising a closure structure to lock in a relative position of said bone screw and said receiver assembly.

14. The spinal anchor assembly of claim 1, wherein the straight edge portion of the D-shaped facet feature is proximal to the curved portion of the D-shaped facet feature.

15. A spinal anchor assembly comprising:
  a bone screw;
  a receiver assembly moveably coupled to the bone screw, the receiver assembly comprising a longitudinal axis; and
  a collar positioned within the receiver assembly, said collar having a first side and a second side opposing the first side, wherein the first side and the second side are straight and parallel to each other, said collar having a third side and a fourth side opposing said third side, wherein the third side and the fourth side are rounded, and wherein the four sides define an inner cavity; wherein said opposing first and second sides each include a D-shaped facet feature on an interior surface thereof facing said inner cavity; wherein said D-shaped facet feature includes a straight edge portion and a curved portion, wherein the bone screw sits in said collar within the receiver assembly with a head of the bone screw pivotably coupled to said curved portion of the D-shaped facet feature, said opposing first and second sides each including an exterior facet feature on an exterior surface thereof, the exterior facet feature facing radially outward from the collar and engaging a surface of the receiver assembly to thereby prevent rotation of the collar within the receiver assembly about the longitudinal axis of the receiver assembly.

16. The spinal anchor assembly of claim 15, wherein said collar, said bone screw, and said receiver assembly are able to articulate relative to each other along a single plane until they are locked into position.

17. The spinal anchor assembly of claim 16, further comprising:
  a closure structure to lock in a relative position of said collar, said bone screw, and said receiver assembly.

18. The spinal anchor assembly of claim 15, wherein the collar further comprises a helical recess on said first side or said second side.

19. The spinal anchor assembly of claim 18, wherein the collar further comprises a plurality of helical recesses on said first side and said second side.

20. The spinal anchor assembly of claim 15, wherein the collar is positioned between the head of the bone screw and the receiver assembly such that the head of the bone screw does not directly engage the receiver.

* * * * *